(12) United States Patent
Curti et al.

(10) Patent No.: US 7,337,780 B2
(45) Date of Patent: *Mar. 4, 2008

(54) NASAL AND ORAL CANNULA BREATHING DETECTION DEVICE

(75) Inventors: James N. Curti, Bakersfield, CA (US); Peter W. Salter, Tehachapi, CA (US)

(73) Assignee: Salter Labs, Arvin, CA (US)

( * ) Notice: Subject to any disclaimer, the term of this patent is extended or adjusted under 35 U.S.C. 154(b) by 320 days.

This patent is subject to a terminal disclaimer.

(21) Appl. No.: 10/861,927

(22) Filed: Jun. 4, 2004

(65) Prior Publication Data

US 2004/0221846 A1    Nov. 11, 2004

Related U.S. Application Data

(60) Continuation-in-part of application No. 10/730,291, filed on Dec. 5, 2003, which is a continuation-in-part of application No. 10/265,527, filed on Oct. 4, 2002, now Pat. No. 6,830,445, which is a division of application No. 09/883,843, filed on Jun. 18, 2001, now Pat. No. 6,533,984, which is a continuation-in-part of application No. 09/754,471, filed on Jan. 4, 2001, now Pat. No. 6,533,983.

(51) Int. Cl.
*A61M 15/08* (2006.01)
*A61M 16/06* (2006.01)

(52) U.S. Cl. .............. 128/207.18; 128/206.11; 128/203.22; 128/200.24; 425/275

(58) Field of Classification Search ............ 425/269, 425/270, 275; 249/184; 128/207.13, 207.15, 128/207.18, 200.24, 206.11, 206.28, DIG. 26, 128/203.22, 203.18, 203.29, 204.12; 600/529, 600/532, 521; 264/219, 221, 304, 305, 327, 264/337, 338

See application file for complete search history.

(56) References Cited

U.S. PATENT DOCUMENTS

| 2,053,357 A | 9/1936 | Winder |
| 2,296,011 A | 9/1942 | Beal |
| 2,824,407 A | 2/1958 | Ebel |
| 2,854,695 A | 10/1958 | Moreau |
| 3,643,660 A | 2/1972 | Hudson et al. |
| 3,731,900 A * | 5/1973 | Havstad ............ 249/177 |
| 3,802,431 A | 4/1974 | Farr |

(Continued)

FOREIGN PATENT DOCUMENTS

| EP | 933094 A2 * | 8/1999 |
| EP | 0 993 094 A2 | 4/2000 |
| FR | 2 197 613 | 3/1975 |
| RU | 1775957 C | 9/1995 |
| RU | 1793628 C | 10/1995 |

OTHER PUBLICATIONS

Salter Labs, "Dual Oral/Nasal ETCO 2 Sampling Cannulas". Copyright 1991, Revised Sep. 2003.

*Primary Examiner*—Justine R. Yu
*Assistant Examiner*—Shumaya B. Ali
(74) *Attorney, Agent, or Firm*—Davis Bujold & Daniels, P.L.L.C.

(57) ABSTRACT

A cannula comprising a main body which defines an internal chamber therein. A first and second nasal prongs, respectively, communicate with the internal chamber to define first and second nasal prong passages. A mouthpiece has a gas passageway and a retainer passageway and a first end of the gas passageway communicates with the internal chamber while a second free end of the mouthpiece has a gas opening therein. A shape retaining member is received within the retainer passageway to facilitate retaining an adjusted position of an opening of the gas passageway with respect to a remainder of the cannula. A method of forming the cannula is also disclosed.

29 Claims, 30 Drawing Sheets

U.S. PATENT DOCUMENTS

| | | |
|---|---|---|
| 3,906,071 A | 9/1975 | Cook et al. |
| 3,931,381 A | 1/1976 | Lindberg |
| 4,106,505 A | 8/1978 | Salter et al. |
| 4,152,688 A | 5/1979 | Dietz |
| 4,433,219 A | 2/1984 | Dietz |
| 4,602,643 A | 7/1986 | Dietz |
| 4,695,241 A | 9/1987 | Ventimiglia |
| 4,745,925 A | 5/1988 | Dietz |
| 4,800,116 A | 1/1989 | Ventimiglia et al. |
| 4,818,320 A | 4/1989 | Weichselbaum |
| 4,878,502 A | 11/1989 | Dietz |
| 5,005,571 A | 4/1991 | Dietz |
| 5,024,219 A | 6/1991 | Dietz |
| 5,038,771 A | 8/1991 | Dietz |
| 5,046,491 A | 9/1991 | Derrick |
| 5,052,400 A | 10/1991 | Dietz |
| 5,074,299 A | 12/1991 | Dietz |
| 5,133,923 A | 7/1992 | Klug |
| 5,335,656 A | 8/1994 | Bowe et al. |
| 5,380,182 A | 1/1995 | Packard et al. |
| 5,485,833 A | 1/1996 | Dietz |
| 5,485,850 A | 1/1996 | Dietz |
| 5,513,634 A | 5/1996 | Jackson |
| 5,682,881 A | 11/1997 | Winthrop et al. |
| 5,922,365 A | 7/1999 | Reichner |
| 6,045,514 A | 4/2000 | Raviv et al. |
| 6,171,258 B1 | 1/2001 | Karakasoglu et al. |
| 6,213,955 B1 | 4/2001 | Karakasoglu et al. |
| 6,217,818 B1 * | 4/2001 | Collette et al. ............. 264/513 |
| 6,247,470 B1 | 6/2001 | Ketchedjian |
| 6,379,312 B2 * | 4/2002 | O'Toole ..................... 600/529 |
| 6,533,983 B2 * | 3/2003 | Curti .......................... 264/219 |
| 6,533,984 B2 * | 3/2003 | Curti .......................... 264/219 |
| 6,635,214 B2 | 10/2003 | Rapacki et al. |
| 6,830,445 B2 * | 12/2004 | Curti .......................... 425/275 |
| 2002/0171175 A1 | 11/2002 | Ainsworth et al. |
| 2003/0030183 A1 * | 2/2003 | Curti .......................... 264/304 |
| 2004/0112383 A1 * | 6/2004 | Curti et al. ............ 128/207.18 |
| 2005/0051176 A1 | 3/2005 | Riggins |
| 2005/0103347 A1 * | 5/2005 | Curti et al. ............ 128/207.18 |

\* cited by examiner

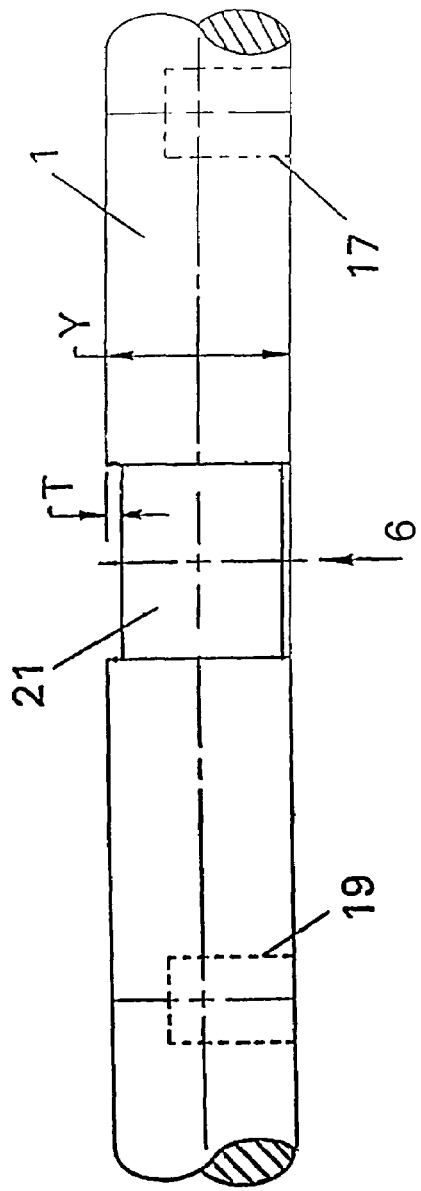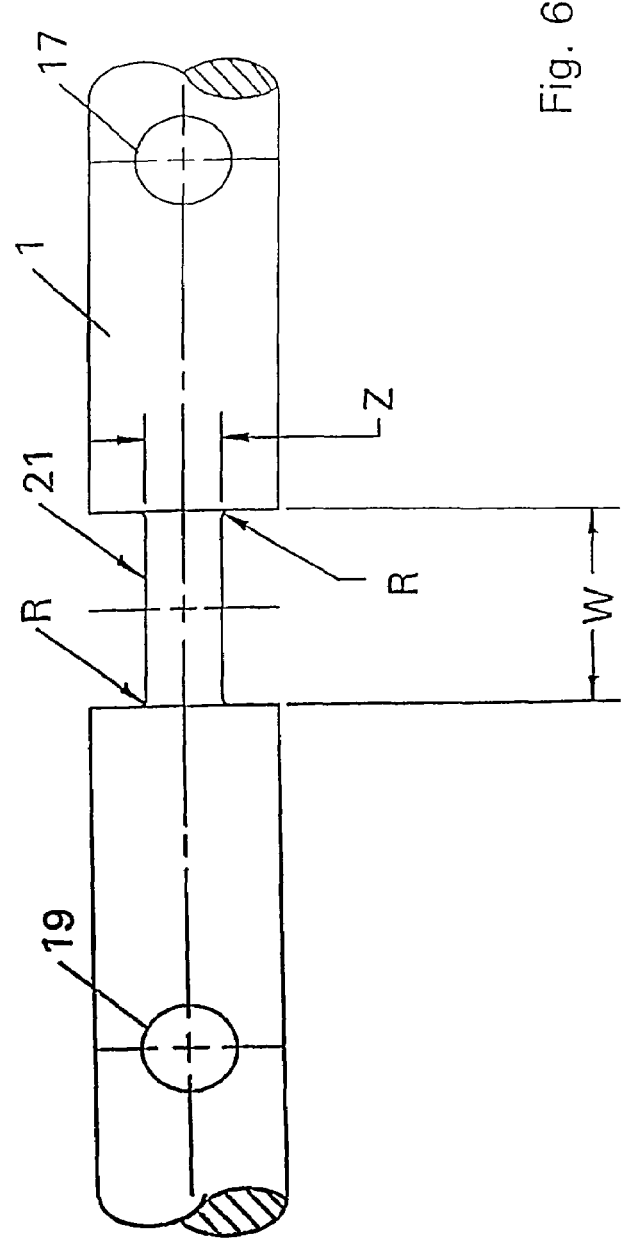

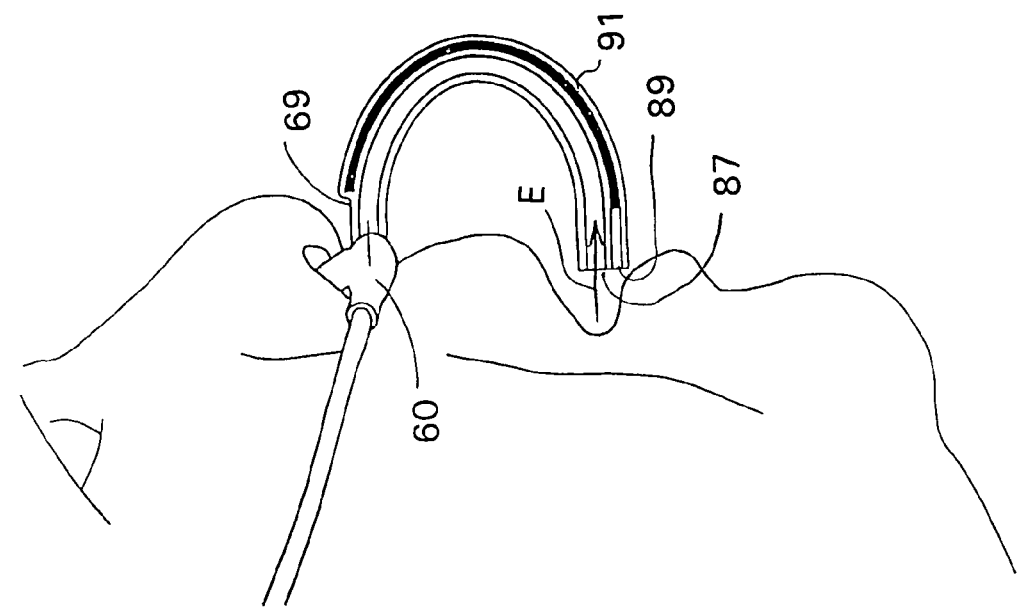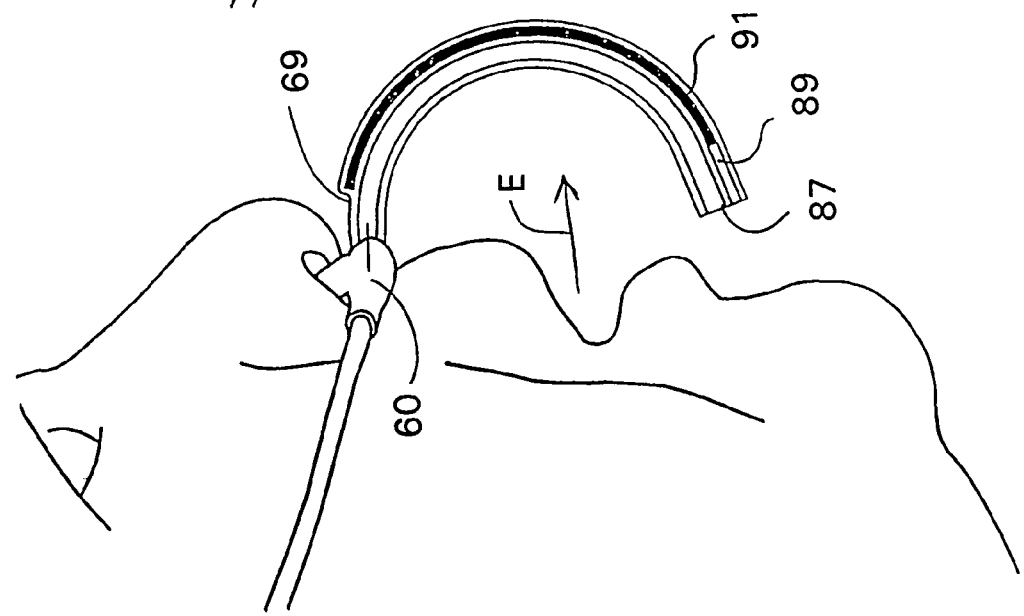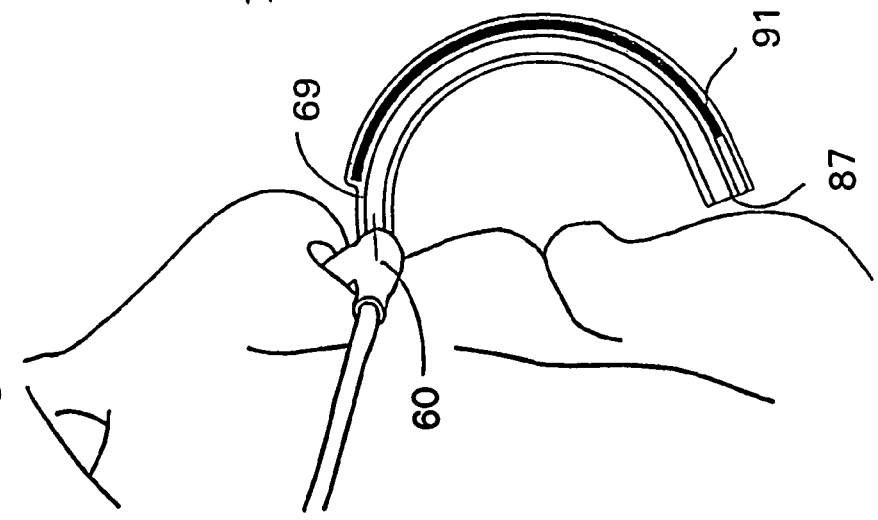

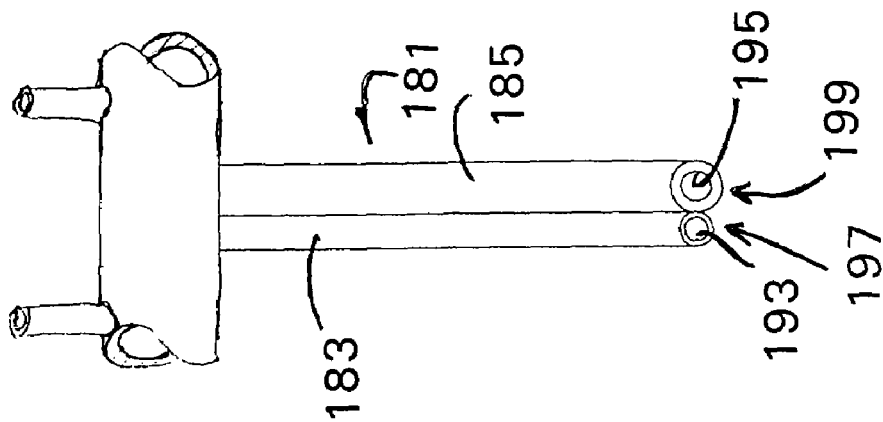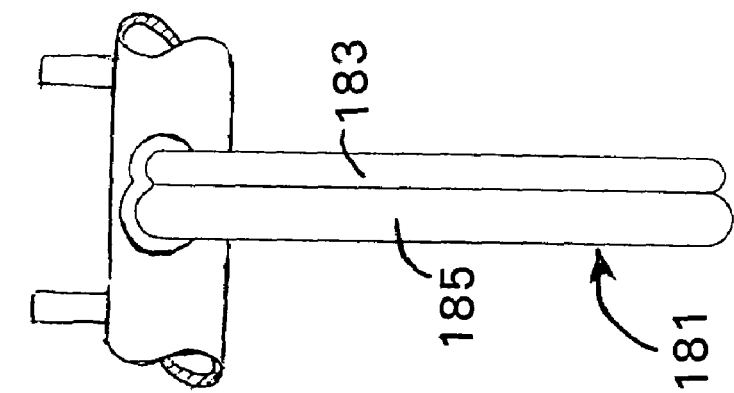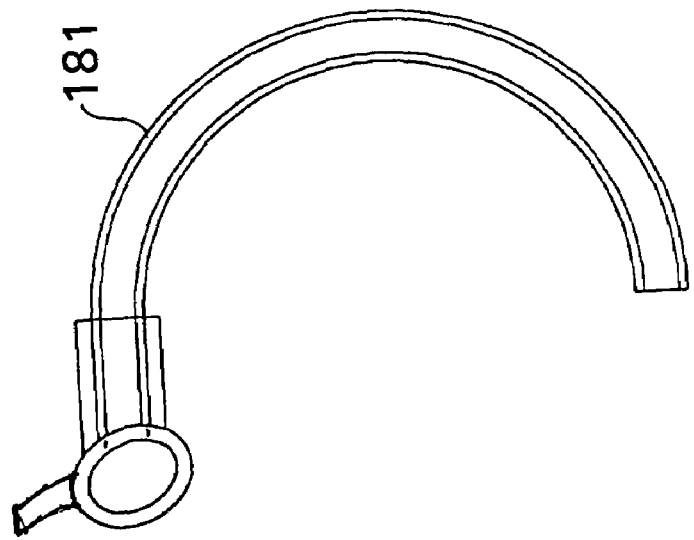

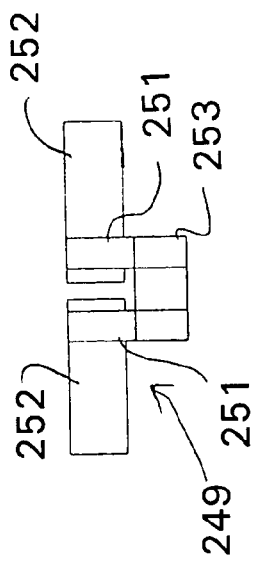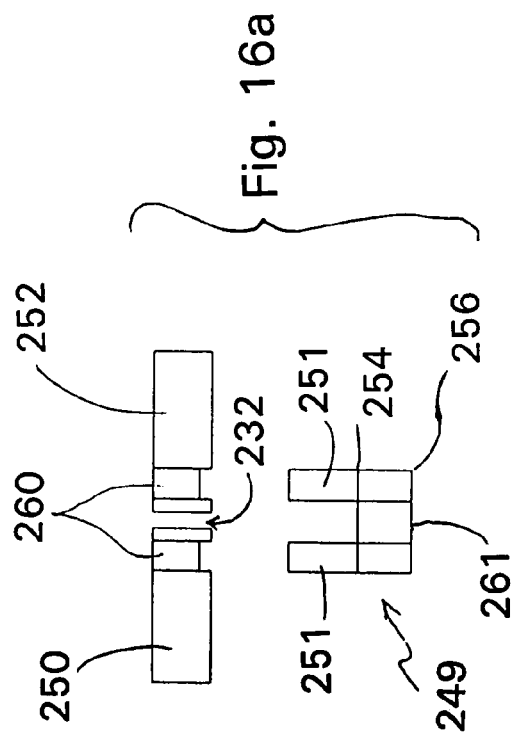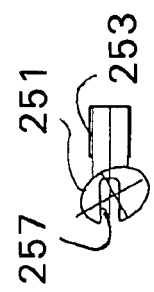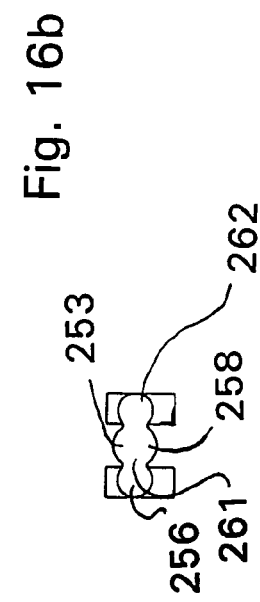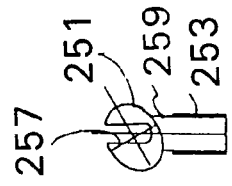

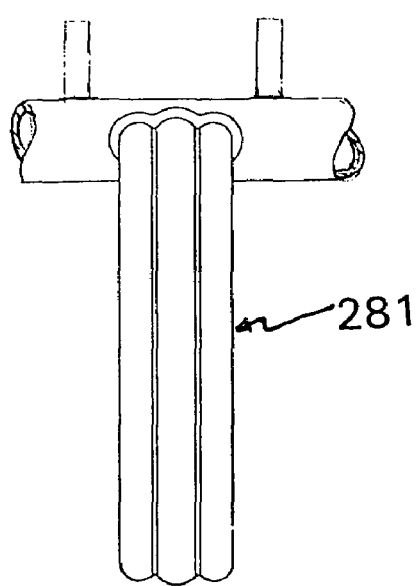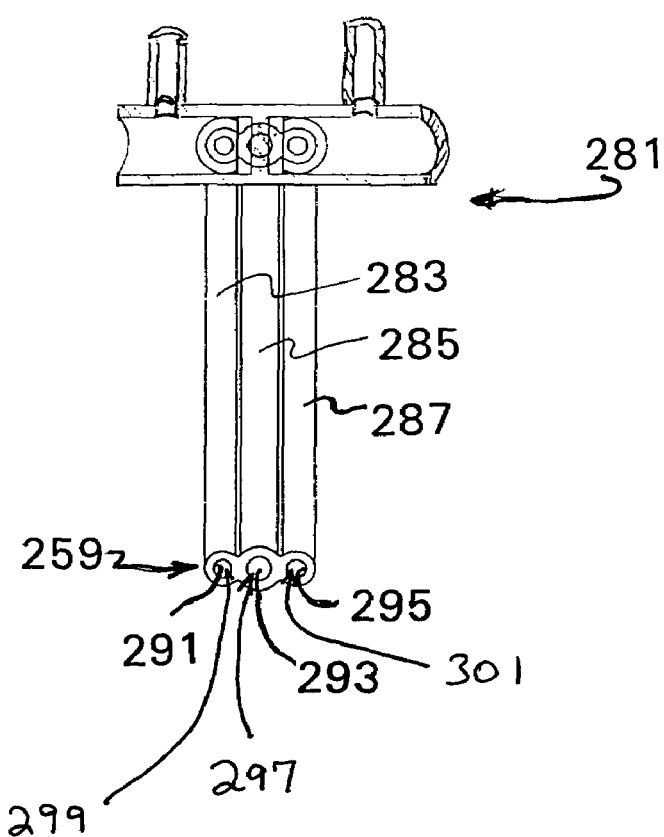

Salter 5007 Pressure & ETCO2
Nose Breathing, Mouth Open

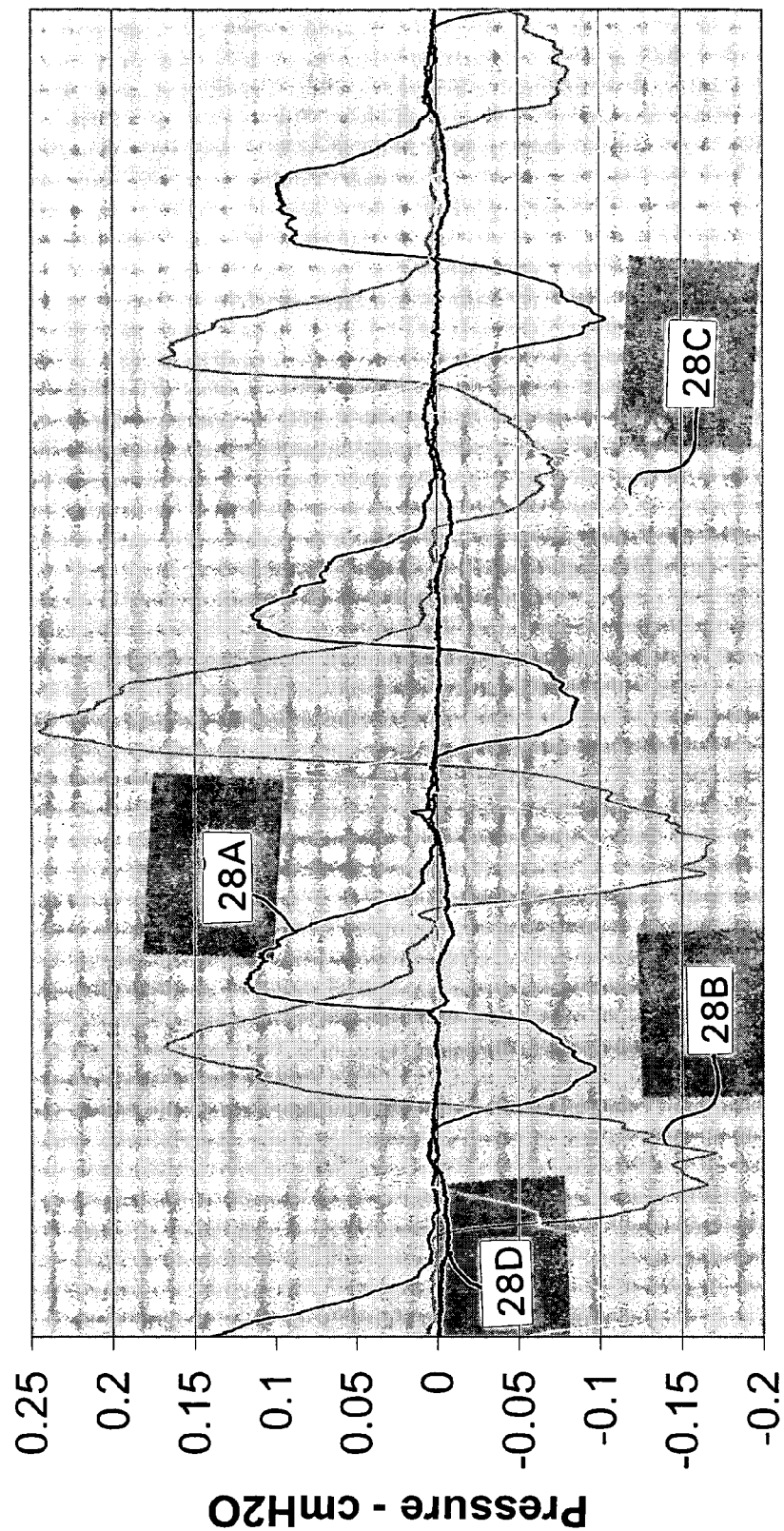
Fig. 28 Salter - 5032 Oral/Nasal Cannula - nasal port

US 7,337,780 B2

NASAL AND ORAL CANNULA BREATHING DETECTION DEVICE

This application is a continuation-in-part application of U.S. application Ser. No. 10/730,291 filed Dec. 5, 2003 which is a continuation-in-part application of U.S. application Ser. No. 10/265,527 filed Oct. 4, 2002, now U.S. Pat. No. 6,830,445 which is a divisional of U.S. application Ser. No. 09/883,843 filed Jun. 18, 2001, now U.S. Pat. No. 6,533,984 which is a continuation-in-part of U.S. application Ser. No. 09/754,471 filed on Jan. 4, 2001 which is now U.S. Pat. No. 6,533,983 dated Mar. 18, 2003.

FIELD OF THE INVENTION

This invention relates to a novel cannula which is suitable for use for both nasal and oral applications and a method of producing the cannula using disconnectable mandrel parts to form a mold over or on which the cannula forming plastics material is applied to form the cannula.

BACKGROUND OF THE INVENTION

This invention relates generally to cannulas adapted for both oral and nasal applications for monitoring breathing of a patient, sampling the end tidal $CO_2$ content in the exhaled breath of a patient to determine the patient's $CO_2$ blood concentration level, or supplying a treating gas, such as oxygen, to a patient. In addition, the invention relates to a method of manufacturing a cannula adapted to interconnect with both nasal passages and the mouth for use to monitor breathing, sample end tidal $CO_2$, supplying a treating gas and is especially suitably for the detection of apnea (the absence of breathing).

Nasal cannulas are commonly used to administer a treating gas, such as oxygen, to humans having respiratory problems. Illustrations of nasal cannulas used for this purpose are found in U.S. Pat. No. 3,802,431. Nasal cannulas have been used also for inhalation therapy, made possible by development of inhalation sensors such as described in U.S. Pat. No. 4,745,925. A nasal cannula can be used to monitor breathing and for detection of apnea when connected to an inhalation sensor.

Nasal cannulas additionally adapted to communicate with the mouth of a patient to permit administration of a gas or sensing of apnea during periods of mouth breathing or nasal blockage are also known.

The present invention relates to a novel cannula and method of manufacturing a cannula having the ability to communicate with both nasal cavities as well as the mouth or oral cavity of a patient. This method provides, in the preferred embodiment, disconnectable mandrels which, when assembled, form a mold over which a cannula forming polymeric material is applied, and which, through the capability of each mandrel component being disconnectable from the other component(s), facilitates removal of the mandrels from the formed or manufactured cannula.

Prior art relating to dipping of a part in a plastisol to create a coating is exemplified by U.S. Pat. Nos. 3,906,071, 4,695,241 and 4,800,116, and the disclosures of those references are hereby incorporated by reference.

SUMMARY OF THE INVENTION

It is an object of the invention to provide a method of manufacturing a cannula using an assembly of disconnectable mandrel components over which cannula forming polymeric material is applied. Application of the plastics material over the mandrel assembly and subsequent extraction of the mandrel components from one another, following sufficient curing of the polymeric material, result in a manufactured cannula with contiguous internal flow paths for sampling the exhaled breath of a patient to detect the end tidal $CO_2$ in the blood of a patient, sensing patient breathing, and/or supplying a treating gas.

It is a further object of the invention to provide a multipart mandrel assembly for forming a cannula which facilitates extraction of each of the mandrel assembly components following at least partial curing the polymeric material forming the cannula.

Still another object of the invention is to form the main body forming mandrel as two separate, slightly spaced apart components which remain spaced apart from one another by a gap or void, during the dipping process, so that the gap void becomes filled with a plastisol to form a septum or barrier which partitions or divides the internal passage of the cannula into two separate compartments or passageways, one which facilitates either sensing of patient breathing, monitoring of the end tidal $CO_2$ in a patient's blood stream or supplying a treating gas while the other of which also facilitates another function, such as, sensing of patient breathing, monitoring of the end tidal $CO_2$ in a patient's blood stream, and/or supplying a treating gas.

Another object of the invention is to produce a cannula having a mouthpiece extending from the main body of the cannula to the patient's mouth, the cannula is provided with a passageway for supplying a gas to the patient via a demand regulator for example, or sampling a patient's oral exhalation for monitoring the end tidal $CO_2$ in a patient's blood stream for instance, and providing the mouthpiece with a retainer passageway for holding a dead soft material enabling the mouthpiece to be bent, shaped, molded or otherwise configured into a desired curvature or orientation for positioning the opening of the mouthpiece in or adjacent the mount or oral cavity of a patient for detecting or sensing the exhaled breath of the patient.

According to the invention there is provided a cannula comprising: a hollow main body having opposed first and second ends, and the main body defining an internal chamber therein; at least a first nasal prong communicating with the internal chamber of the main body and defining a first nasal prong passage; a mouthpiece having a gas passageway and a retainer passageway, a first end of the gas passageway communicating with the internal chamber of the main body while a second free end of the mouthpiece having a gas passageway opening therein; and an elongate shape retaining member having a first end and a second end, the shape retaining member being received within the retainer passageway with the first end of the shape retaining member located adjacent the main body and the second end of the shape retaining member being located adjacent the second free end of the mouthpiece.

Also according to the invention there is provided a method of forming a cannula comprising the steps of providing cannula mandrel assembly parts, said parts comprising a pair of nare forming mandrels, a main body forming mandrel having a central rectangular recessed section and openings to receive and engage ends of the nare forming mandrels, and a mouthpiece forming mandrel having an end connector, the end connector defining a slot dimensioned to mate slidingly with the rectangular recessed section; assembling the parts to provide a cannula mandrel assembly defining interior spaces of the cannula; heating the cannula mandrel assembly to a desired temperature; providing a cannula forming polymeric material as a plastisol; dipping the heated cannula mandrel assembly in the plastisol to provide a desired thickness of partially cured polymer on the cannula mandrel assembly to form the cannula; heating the cannula material of the cannula to further cure the cannula material; and extracting the nare forming mandrels, the mouthpiece forming mandrel by removing the slot from the rectangular recess, and the main body forming mandrel from the cannula.

Also according to the invention there is provided a method of manufacturing a nasal cannula comprising the steps of: assembling a cannula mandrel assembly comprising separable components with the separable components including a main body forming mandrel, at least one nare forming mandrel, and a mouthpiece forming mandrel; heating the assembled cannula mandrel assembly to a desired temperature; applying at least one coating of an uncured cannula forming polymeric material to the cannula mandrel assembly to provide a desired material thickness of coating on the cannula mandrel assembly; sufficiently curing the coating applied to the cannula mandrel assembly; and disassembling the cannula mandrel assembly and withdrawing the at least one nare forming mandrel, and mouthpiece forming mandrel and the main body forming mandrel from the manufactured cannula.

Also according to the invention there is provided a cannula mandrel assembly, defining the internal chamber of a cannula having a main body, a nare and a mouthpiece, comprising an elongate nare forming mandrel; an elongate mouthpiece forming mandrel; and an elongate main body forming mandrel defining a recessed rectangular section slidably receiving, engaging and supporting a connector end feature of the mouthpiece forming mandrel and defining a transverse opening receiving, engaging and supporting an end of the nare forming mandrel.

BRIEF DESCRIPTION OF THE DRAWINGS

The invention will now be described, by way of example, with reference to the accompanying drawings, in which:

FIG. 5 is a fragmentary side elevation of the main body mandrel of FIGS. 1 and 2 taken along section line 5-5 of FIG. 2;

FIG. 6 is an elevation of the main body mandrel taken in the direction of arrow 6 in FIG. 5;

FIGS. 12A and 12B, respectively, are side elevational views showing the originally molded orientation of the mouthpiece relative to a close and an open mouth of a patient while FIG. 12C is side elevational view showing retained adjusted orientation of the mouthpiece, relative to an open mouth of a patient, for aligning an opening of the mouthpiece with the patient's oral inhalation/exhalation path;

FIG. 15E is a diagrammatic transverse cross sectional view of a completed cannula manufactured by the mandril stub of FIGS. 15A and 15B;

FIG. 15F is a diagrammatic front elevational view of the manufactured cannula of FIG. 15E;

FIG. 15G is a diagrammatic rear elevational view of the manufactured cannula of FIG. 15E;

FIG. 16A is a diagrammatic plan view showing a modification to the mandril stub prior to attachment to the main body mandrel;

FIG. 16B is a diagrammatic end view of the mandril stub of FIG. 16A taken along section 16B-16B of FIG. 16A;

FIG. 16C is a diagrammatic plan view showing of the modified mandril stub of FIG. 16A shown assembled with the main body mandrel comprising two separate components;

FIG. 16D is a diagrammatic right side view of the mandril stub of FIG. 16B;

FIG. 16E is a diagrammatic left side view of the mandril stub of FIG. 16B;

FIG. 18A is a diagrammatic front elevational view of a completed cannula manufactured from the facepiece of FIGS. 17A and 17B;

FIG. 18B is a diagrammatic rear elevational view of the manufactured cannula of FIG. 18A;

FIG. 28 is a graph displaying additional test results, generated by a single port cannula, showing the detected breathing pressure for different breathing styles of the patient.

DETAILED DESCRIPTION OF THE EMBODIMENTS

Figure 1:
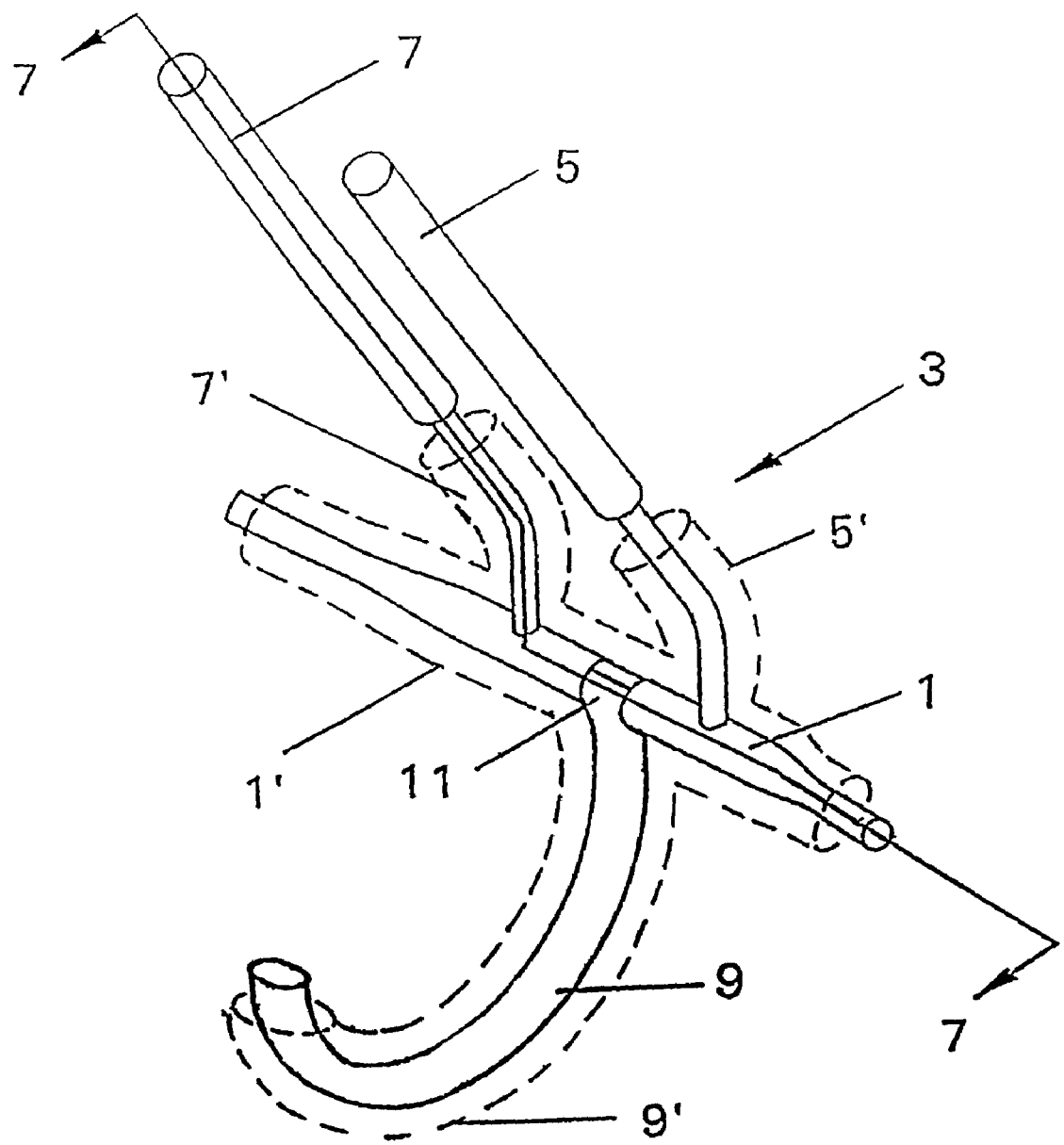
FIG. 1 is an orthogonal view of a cannula mandrel assembly with cannula forming polymeric material shown in ghost.

Referring to FIG. 1, the main body forming mandrel 1 of a beryllium copper cannula mandrel assembly 3 is shown with a pair of spaced apart nare forming mandrels 5 and 7, and a separate mouthpiece forming mandrel 9 having an end connector 11 for joining the mouthpiece mandrel 9 to the main body forming mandrel 1. A cannula 2', to be formed on the assembly, is shown in ghost and such cannula generally comprises a main body 1', a pair of nares 5', 7' and a mouthpiece 9' composed of polyvinyl chloride (PVC), for example.

Figure 2:
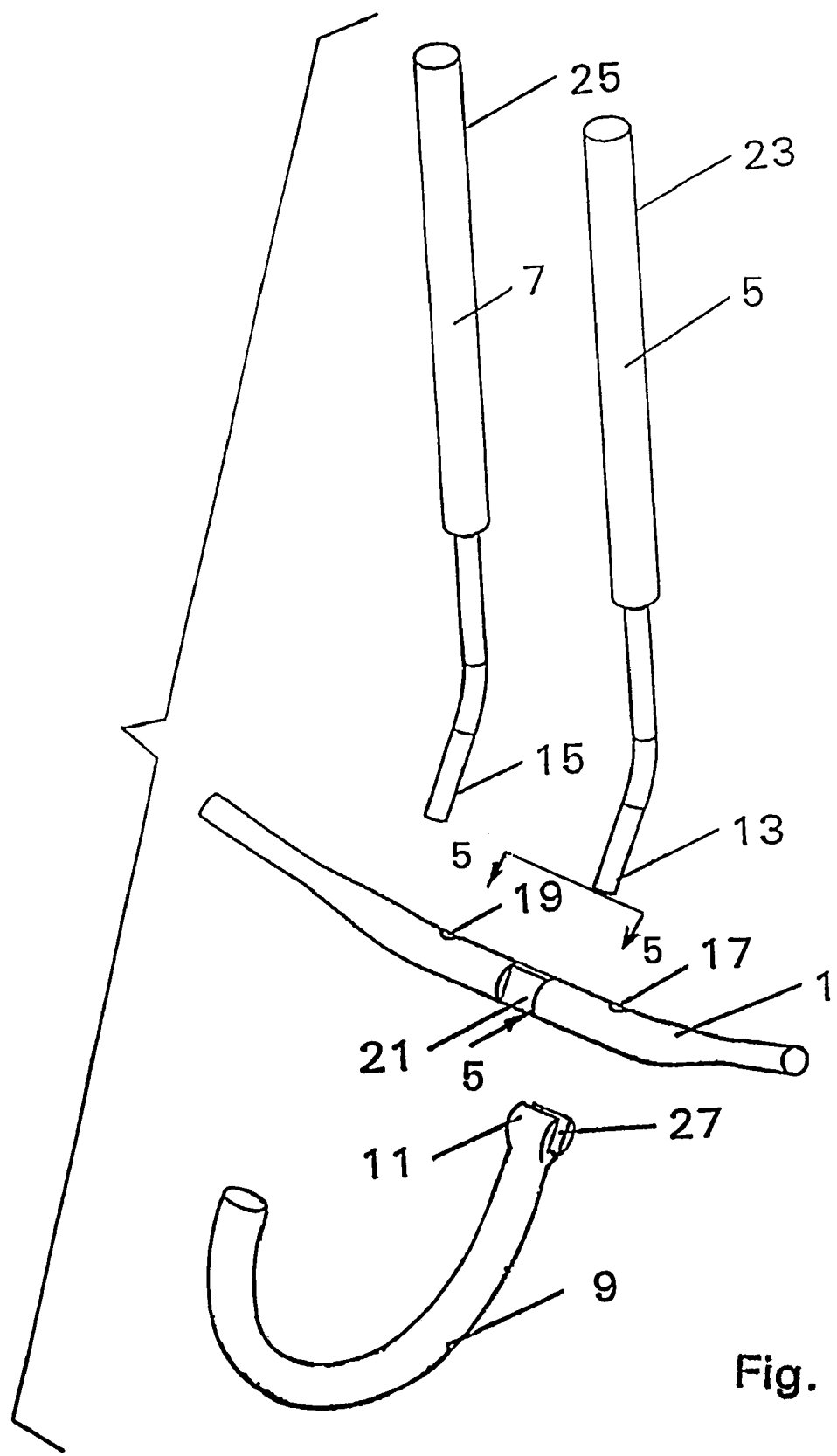
FIG. 2 is an orthogonal view of the cannula mandrel parts prior to assembly.

FIG. 2 shows the mandrel assembly components prior to assembly in order to form or produce the cannula mandrel assembly 3. Each of the nare mandrels 5 and 7 has a reduced diameter section 13 or 15 which form nares 5', 7', respectively, over which cannula forming polymeric material is applied. Reduced diameter sections 13 and 15 of nare mandrels 5 and 7 matingly slide into and are received by respective blind holes 17 and 19 of main body mandrel 1. Main body mandrel 1 also has a central rectangular recessed section 21 which slidably mates and receives the end connector 11 of mouthpiece mandrel 9.

Nare mandrels 5 and 7 also have enlarged diameter sections 23 and 25 which support a plurality of identical cannula mandrel assemblies 3 in a jig (not shown) during the molding process. Additionally, the enlarged diameter enables sections 23 and 25 provide a larger contact surface which allows easier gripping of nare mandrels 5 and 7 to facilitate removal of the nare mandrels 5 and 7 from main body mandrel 1 after partial curing of the PVC, or some other plastisol or plastics material, on the cannula mandrel assembly 3.

FIG. 2 further shows the mouthpiece mandrel 9 with the end connector 11 which has a centrally located slot 27 which slidably engages with the rectangular section 21 of the main body mandrel 1. Slot 27 is sized to permit close contact or engagement of the slot 27 with the rectangular section 21 of main body mandrel 1 such that a snug fit or attachment is obtained so as to removably retain the mouthpiece mandrel 9 on the main body mandrel 1 while also facilitating extraction of the mouthpiece mandrel 9 from the rectangular section 21 following partial curing of the PVC, or some other plastisol or plastics material, on the cannula mandrel assembly 3. The outer surface of end connector 11 is sized to approximate a continuation of the outer surface or diameter of main body mandrel 1 to provide a substantially uniform amount of applied PVC, or some other plastisol or plastics material, to the cannula mandrel assembly 3 and still facilitate withdrawal of the mouthpiece mandrel 9 from the cannula mandrel assembly 3 and the mouthpiece 9' of the cannula.

Figure 3:
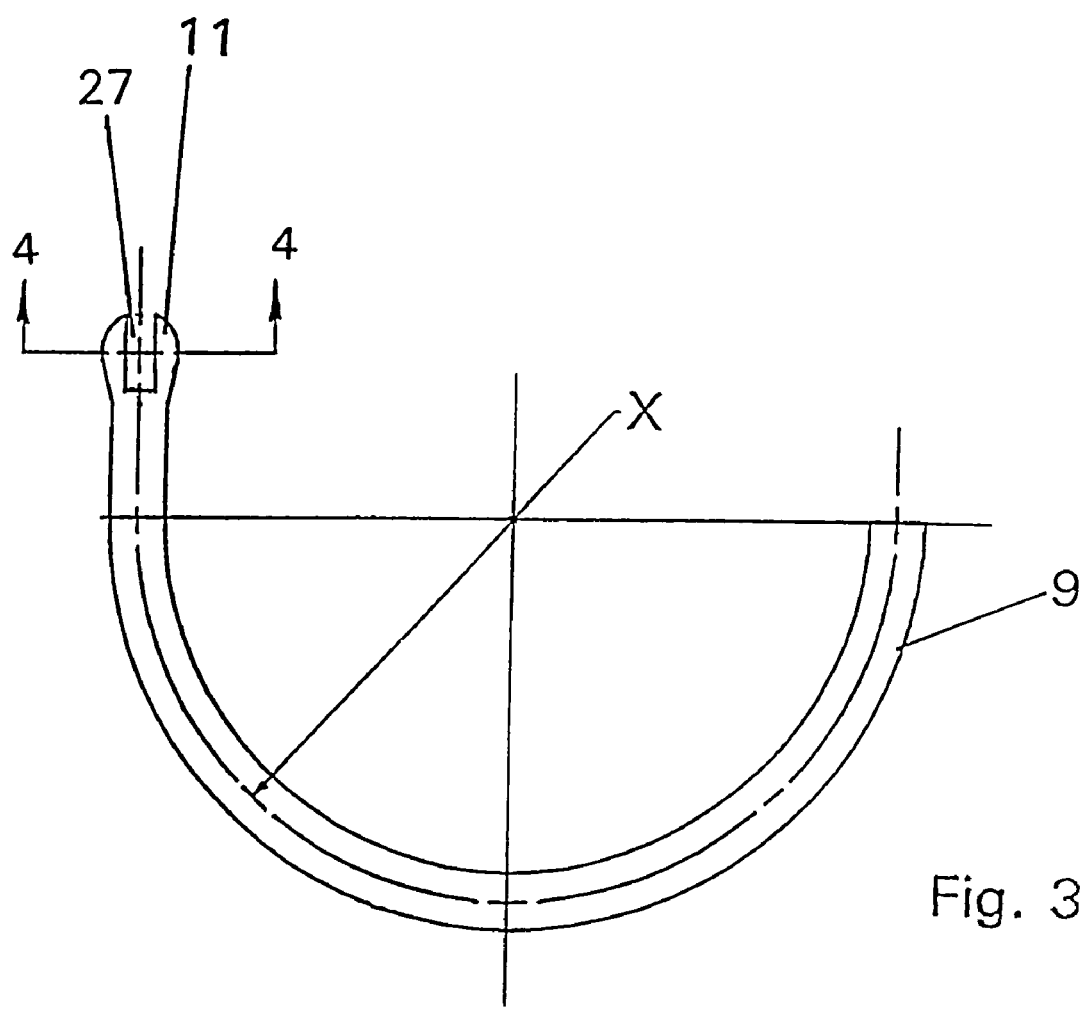
FIG. 3 is a side elevation of the mouthpiece mandrel of FIGS. 1 and 2 showing an end connector.

FIG. 3 shows the general contour of the mouthpiece mandrel 9 having a desired radius X with the end connector 11 located at one end of the mouthpiece mandrel 9 and having a slot 27 formed in the end connector 11.

Figure 4:
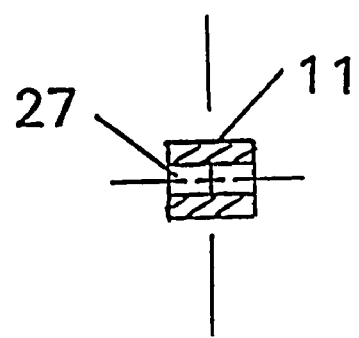
FIG. 4 is an end section of the end connector taken along section line 4-4 of FIG. 3.

FIG. 4 is a view along section line 4-4 of FIG. 3 which shows the shape, e.g., the length, the width, and the thickness, of the end connector 11 and the slot 27.

Referring to FIGS. 5 and 6, a pair of spaced apart blind holes 17 and 19 are formed in a central region of the main body mandrel 1. Each blind hole 17 and 19 is sized to matingly receive, via a sliding fit, one of the reduced diameter sections 13 or 15 of the nare mandrels 5 and 7 in order to engage and support nare mandrels 5 and 7 in a proper molding orientation during application of the PVC, or some other plastisol or plastics material, to the cannula mandrel assembly 3 for formation of the cannula 2'. The rectangular section 21 is made with a shoulder depth T removed to allow the diameter of end connector 11 of mouthpiece mandrel 9 to mate approximately flush with the diameter Y of main body 1.

The rectangular section 21 is shown preferably with a relieving radii R at opposed ends of the section. The relief radius R may be omitted if the main body mandrel 1 is machined or formed in a manner that allows this. Thickness Z of rectangular section 21 permits slot 27 of end connector 11 of mouthpiece mandrel 9 to firmly but slidably mate with rectangular section 21 and adequately maintain the engagement between those two components with one another during dipping. Width W of rectangular section 21 is just sufficient to closely accommodate end connector 11 of mouthpiece mandrel 9, e.g., a very small clearance fit between those two components is provided.

FIGS. 1 and 2 show nare mandrels 5 and 7 with bend sections 12 and 14. These bend sections 12 and 14 sufficiently curve or direct the nares of the cannula 2', following manufacture of the cannula, so that the nares may be properly aligned to be received within a patient's nasal cavities.

Although beryllium copper is the preferred material for manufacture of the cannula mandrel assembly 3, other materials which possess appropriate working temperature ranges, retain dimensional stability for reuse in a manufacturing environment and will easily and readily release the cannula 2' after curing of the following partial curing of the PVC, or some other plastisol or plastics material, may be used. Metals including, but not limited to, steel, aluminum, bronze, brass, and copper alloys may be used, as well as some plastics materials. Beryllium copper is preferred due to its ability to transfer heat rapidly and reliably release the cured PVC, plastisol or other plastics material formed on the cannula mandrel assembly 3. Rapid heat transfer is desirable for the mandrel material both during heating of the cannula mandrel assembly 3 and following application of the cannula forming polymeric material where a partial cure of the polymeric material is followed by rapid cooling.

Prior to application of a plastisol solution, such as PVC, the cannula mandrel 3 is coated, usually by dipping step or process, with a silicone release layer or agent to facilitate separation and/or removal of the mandrel components from the plastisol to be applied. The application of the plastisol, in the preferred embodiment, is by dipping the silicone coated cannula mandrel assembly 3 which has been heated in an oven at an oven temperature of from about 350° F. to about 550° F. (preferably about 45° F.) for about 1 to about 3 minutes prior to dipping in a plastisol solution of PVC. One or more dipping steps may be performed to achieve the desired finished cannula material thickness and each of these dipping steps may be for a duration of 10-30 seconds, for example. During dipping, the mandrel is supported by the outer end portions of the nare mandrels.

The preferred use of a plastisol solution of PVC provides a semi-clear finished cannula with sufficient strength to withstand subsequent attachment of various connectors while still being sufficiently flexibility to prevent injury or irritations to the user. Alternatively, other plastics materials, which have material properties suitable for this method, capable of forming a plastisol, may be substituted for PVC.

Partial curing of the cannula takes place on the mandrel assembly 3. The cannula mandrel assembly with the partially cured PVC thereon is then placed in an oven, for a sufficient time, for further curing at a temperature from about 410° F. to about 450° F. Following curing to stabilize the PVC and after the cannula has sufficiently cooled to allow mandrel removal with the assistance of the release layer or agent, without damaging the cannula, while providing sufficient physical strength to retain cannula shape, the mandrel components are then removed from the manufactured cannula.

Using the inventive method, a cannula with two nares and a mouthpiece is formed as follows: a cannula mandrel assembly 3 is formed by first, slidably mating reduced diameter sections 13 and 15 of nare mandrels 5 and 7 with the blind holes 17 and 19, respectively, of the main body mandrel 1; second, orienting nare mandrels 5 and 7 so that they are properly aligned as shown in FIG. 1; third, slidably mating the slot 27 of the end connector 11 of the mouthpiece mandrel 9 with the rectangular section 21 of the main body mandrel 1 in a desired orientation relative to the nare mandrels 5 and 7 so that it is also properly aligned as shown in FIG. 1; fourth, providing a silicone release layer or agent substantially encompassing the mandrel components; fifth, heating the assembled cannula mandrel assembly in an oven at a temperature of from about 350° F. to about 550° F.; sixth, providing a liquid uncured plastisol mix (PVC); seventh, dipping the cannula mandrel assembly into the liquid uncured plastisol mix (PVC), at least once, until the desired material thickness is built-up and/or achieved on the mandrel assembly 3; eighth, at least partially curing the PVC at a temperature of about 410° F. to about 450° F.; and ninth, following sufficient curing, removing the nare mandrels 5 and 7 from the blind holes 17 and 19 of main body mandrel 1 and the nares 5', 7' by pulling on enlarged diameter sections of the nare mandrels 5 and 7, and removing the mouthpiece mandrel 9 from the mouthpiece 9' by disengaging the slot 27 of the end connector 11 from the rectangular section 21 of the main body mandrel 1 and pulling the mouthpiece mandrel 9 out through the mouthpiece 9'; and finally slidably removing main body mandrel 1 from the main body 1' of the cannula by extracting or withdrawing the same from one end of the manufactured cannula 2'.

Figure 7:
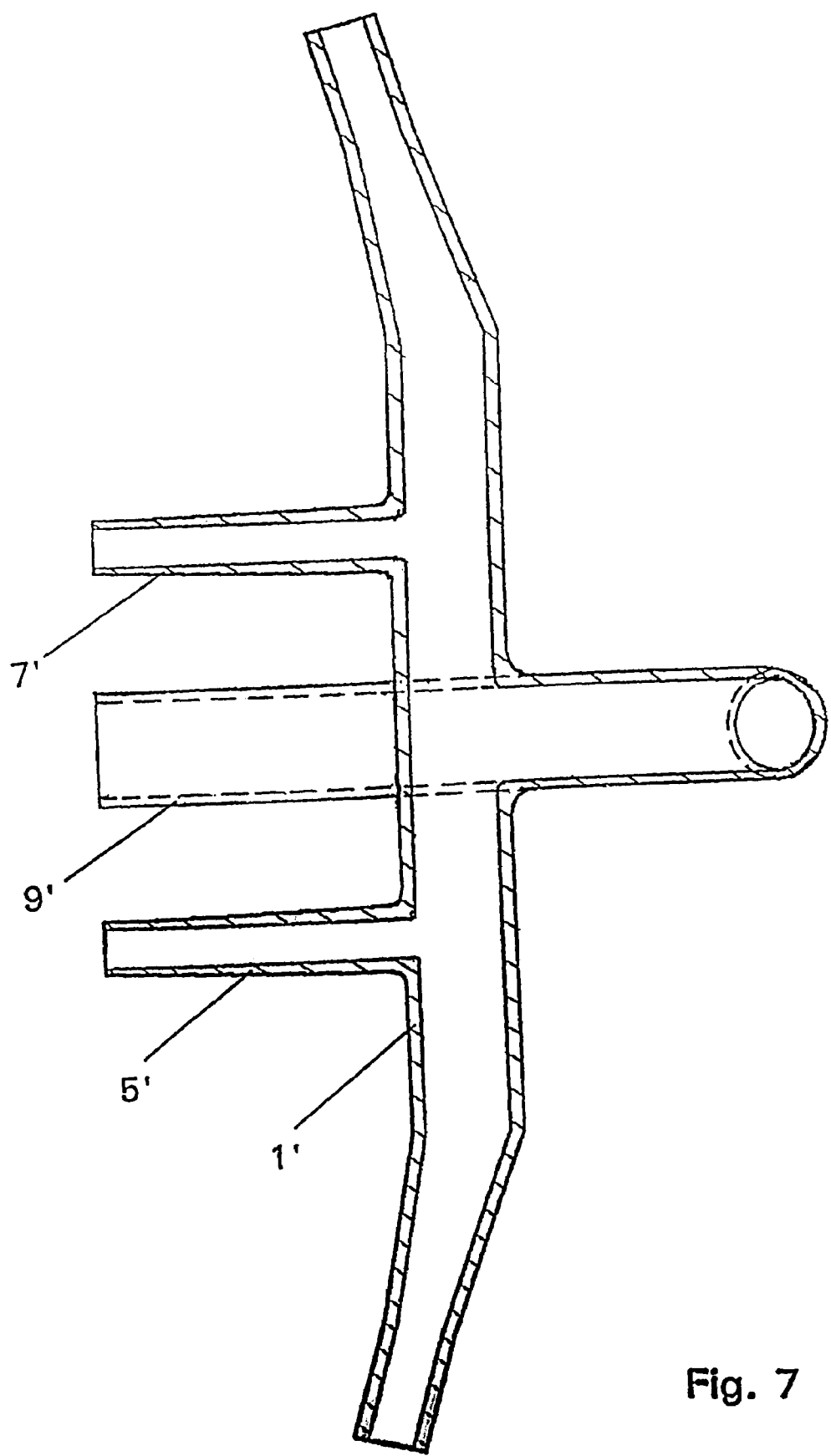
FIG. 7 is a general diagrammatic cross-sectional view of a cannula, made by the method of the present invention, taken along section line 7-7 of FIG. 1.

FIG. 7 shows a diagrammatic cross sectional view of a finished or manufactured cannula, following removal of the components of the cannula mandrel assembly 3 from the cured PVC cannula, and the formed contiguous flow paths through the main body 1', the nares 5' and 7' and the mouthpiece 9' can be seen.

It will be appreciated that the curing step may be completed in two stages, namely, a first partial cure of the PVC produced by the heated cannula mandrel assembly 3 which is sufficient to maintain the PVC on this assembly and a second stage in an oven at the above indicated curing temperatures to complete curing, following the partial curing of the PVC, the plastisol or some other plastics material.

It will be further appreciated that the opposed outer ends of the main body 1' of the manufactured cannula may be trimmed, as necessary or desired, to provide a discrete area where a flexible connecting tubing or conduit may be connected thereto, e.g., by solvent bonding with MEK (methyl ethyl ketone) for example, and the mouthpiece 9' may be trimmed to a desired length suited to an individual patient so as to maximize the sensitivity of the finished device.

It will also be understood that disassembly of the cannula mandrel assembly 3, following curing of the cannula forming polymeric material, can proceed by removing the mouthpiece mandrel before the nare mandrels as an obvious alternative method step, prior to removal of the main body mandrel.

One modification of the present invention relates to the addition or formation of a septum in the internal passage of the cannula 2' to provide an internal partition or barrier therein, e.g., form a "divided cannula." The septum 29 divides the internal chamber C of the main body 1' of the cannula 2' into two separate compartments or passageways C1 and C2 so that a first one of the nares 5' can be coupled to a treating gas, such an oxygen source (not shown), to facilitate the supply of supplemental oxygen to one of the nostrils of a patient while the other one of the nares 7' and the central mouthpiece 9' can be coupled to a monitoring device (not shown), such as a transducer, to facilitate monitoring of breathing of the patient or coupled to a demand oxygen conserving device (not shown) while the patient, at the same time, is still able to receive, either continuously or intermittently during the sensed breathing cycle, a supplemental supply of oxygen. Alternatively, one of the nares 5' can be connected to a capnograph, for example, to sample the exhaled breath of a patient and detect the end tidal $CO_2$ in the blood stream of a patient.

In order to manufacture the septum 29, the main body forming mandrel 1 is formed as first and second separate, slightly spaced apart mandrel components 30, 31 which remain spaced apart from one another by a small gap or void 32 following assembly of the cannula mandrel assembly 3 and during the dipping operation of the manufacturing process so that the void 32 between the first and the second separate, slightly spaced apart mandrel components 30, 31 is filled with PVC, or some other plastisol or plastics material, and forms the septum 29. Once the cannula is adequately cured, the septum 29 forms a partition or barrier within the main body 1' of the cannula which divides the internal chamber C into two separate compartments or passageways C1 and C2.

Following sufficient curing, the nare mandrels 5 and 7 are removed from the blind holes 17 and 19 of main body mandrel 1 and the nares 5', 7' by pulling on enlarged diameter sections of nare mandrels 5 and 7, the mouthpiece mandrel 9 is removed from the mouthpiece 9' by disengaging the slot 27 of the end connector 11 from the rectangular section 21 of the main body mandrel 1 and pulling the mouthpiece mandrel 9 out through the mouthpiece 9'; and the first and second spaced apart components 30, 31 of the main body mandrel 1 are removed from the main body 1' of the cannula by pulling the first and second spaced apart components 30, 31 axially away from one another and out from the main body 1' of the cannula 2'.

This variation of the manufacturing process is suitable for intermittent nocturnal oxygen delivery even though the patient breaths through his or her mouth.

Figure 10A:
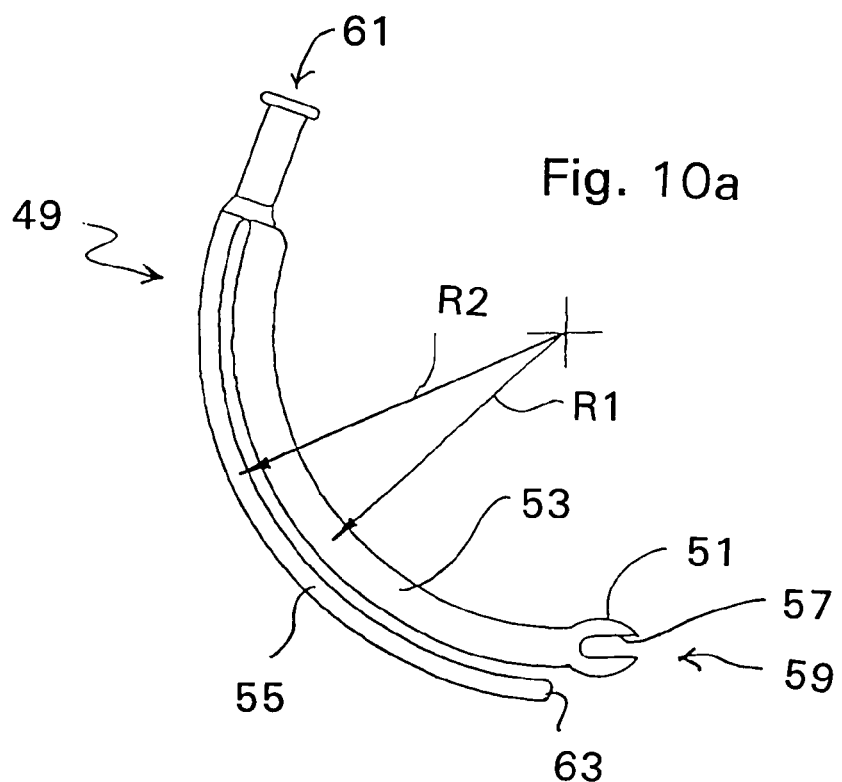
FIG. 10A-C are a front elevational, a bottom and a left side elevational views, respectively, of the mouthpiece mandrel showing the gas passage prong and the retainer prong.
Figure 10B:
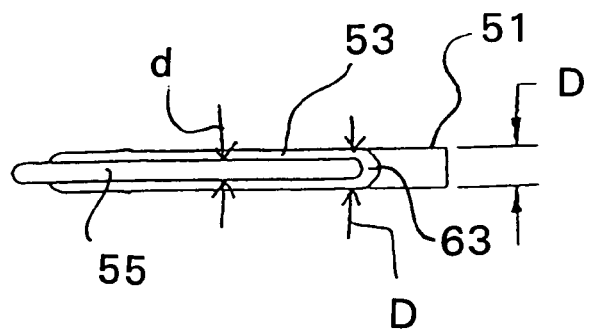
Figure 10C:
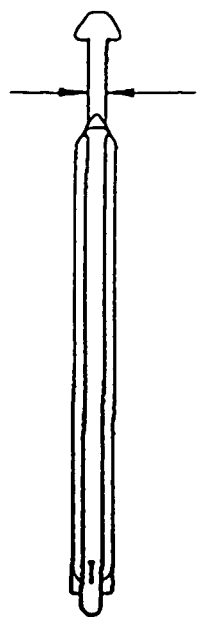

Another embodiment of the present invention provides the cannula mandrel assembly 3 with a divided mouthpiece mandrel 49 as shown in FIGS. 10A-C. The mouthpiece mandrel 49 comprises a gas passage prong 53 for forming a gas passageway in the mouthpiece of the manufactured cannula, and a retainer prong 55 for forming a retainer channel, lumen or passageway or cavity to receive a malleable shape retaining member or dead soft material. The shape retaining or dead soft material permits the mouthpiece to be bent, configured or molded into a desired shape, configuration or position while still retaining such desired shape, configuration or position following adjustment of the mouthpiece. A further description of these features of the present embodiment follows below.

As with previous embodiments, in order to attach the mouthpiece mandrel 49 to the main body mandrel 1, the mouthpiece mandrel 49 includes an end connector 51 attached to a connecting end 59 of the gas passage prong 53. The end connector 51 has a centrally located slot 57 which slidably engages or receives the rectangular section 21 of the main body mandrel 1, as described above. The slot 57 is sized to permit close contact and engagement thereof with the rectangular section 21 of main body mandrel 1 such that a snug fit and retention of the mouthpiece mandrel 49 with the main body mandrel 1 is obtained during dipping while still facilitating extraction of the mouthpiece mandrel 49 from rectangular section 21 following partial curing and cooling of the PVC, or some other plastisol or plastics material. As with the other embodiments, the outer surface of end connector 51 has a shape and size which approximates the outer diameter of the main body mandrel 1 to provide a uniform diameter of applied cannula forming polymeric material while also facilitating withdrawal of the mouthpiece mandrel 49 from the mouthpiece 69 of the manufactured cannula (see FIG. 11).

At a free end 61 of the mouthpiece mandrel 49, the respective ends of the gas passage prong 53 and the retainer prong 55 are structurally joined or fixedly connected with one another so that the retainer prong 55 is integral with and supported by the gas passage prong 53. The gas passage prong 53 and the retainer prong 55 extend substantially parallel to one another along concentric radii of curvature R1, R2 from the free end at which these two components are joined with one another to the opposite connecting end 59 of the mouthpiece mandrel 49. These radii of curvature R1 and R2 can vary but are generally chosen to facilitate the functional alignment of the cannula mouthpiece with a patient's open mouth. For example, these radii of curvature can range from between about 0.5 of an inch to about 2.5 inches or so, and more preferably can range from between about 0.75 of an inch to about 2.0 inches with radius R1 being slightly smaller than R2, e.g., smaller by ⅛ to ¼ of an inch or so. The separation between the gas passage prong 53 and the retainer prong 55 forms a uniform elongate spacing or area between those to prongs such that a sufficient space is provided so that during the dipping operation(s), which applies a plastisol coating to the cannula mandrel assembly 3, no air pocket(s) or void(s) are formed in the plastisol which flows into the elongate area between the gas passage prong 53 and the retainer prong 55.

As can be seen, although the end connector 51 is attached to one end of the gas passage prong 53, the retainer prong 55, however, merely terminates at a free end 63 adjacent the end connector 51 of the mouthpiece mandrel 49. The free end 63 of the retainer prong 55 is spaced a sufficient distance from the end connector 51 of the mouthpiece cannula 49 so as to eliminate formation of any air pocket(s) or void(s) during the dipping operation(s) between the free end 63 of the retainer prong 55 and the end connector 51 and/or the main body mandrel 1.

Observing FIG. 10B, the retainer prong 55 may be formed with an outer diameter d sized for forming a lumen or passageway in the mouthpiece 69 for receiving and snugly accepting a retaining or dead soft material for maintaining a change in the shape, orientation, form and/or curvature of the mouthpiece 69. By way of explanation, the retaining or dead soft material has substantially no structural memory of any previous shape, orientation, configuration or form which would cause the material to retain, return or spring back to such previous shape, orientation, configuration or form. A suitable example of the retaining or dead soft material, to be used as a shape retaining support in the manufactured cannula, is copper wire, either insulated or uninsulated, although other dead soft materials, for example, other metals or plastics materials, would also be suitable. Copper is a highly malleable metal and generally retains whatever shape is imparted thereto at any particular time without reverting or returning back to any prior or previous shape. Copper is also a preferred dead soft material, over for example iron, steel or other ferromagnetic materials, due to the propensity of the nasal cannula to be used on a patient exposed to certain electromagnetic and magnetic environments and/or diagnosis procedures.

The thickness or outer diameter D of the gas passage prong 53 may be larger in size than the thickness of diameter d of retainer prong 55 due to fact that the gas passageway in the cannula generally must be larger in size to provide an adequately sized gas flow passageway within the mouthpiece 69 of the cannula to supply a desired treating gas to a patient, for example, via a demand regulator to a mouth breathing patient. Alternatively, the gas passageway formed by the gas passage prong 53 must be of sufficient size to allow withdrawal, detection or sampling of exhalation gases from a mouth of a breathing patient.

The above described mouthpiece mandrel 49 is assembled with a pair of nare mandrels and the main body mandrel to form the cannula mandrel assembly 3. Following dipping and curing, the interior spaces and passages of the cannula including the passage or cavity 79 for receiving the dead soft material. The cannula mandrel assembly is pre-heated to a desired temperature, and dipped in the cannula forming polymeric plastisol to provide a desired thickness of partially cured polymer on the cannula mandrel assembly 3 and produce the manufactured cannula. The cannula forming polymeric material is again heated in an oven to further cure the cannula forming polymeric material, as previously described. Finally, both of the nare forming mandrels, the mouthpiece forming mandrel 49, including both the gas passage prong 53 and the retainer prong 55, as well as the main body forming mandrel 1 are extracted to result in the manufactured and cured cannula 60 shown in FIG. 11.

Figure 11:
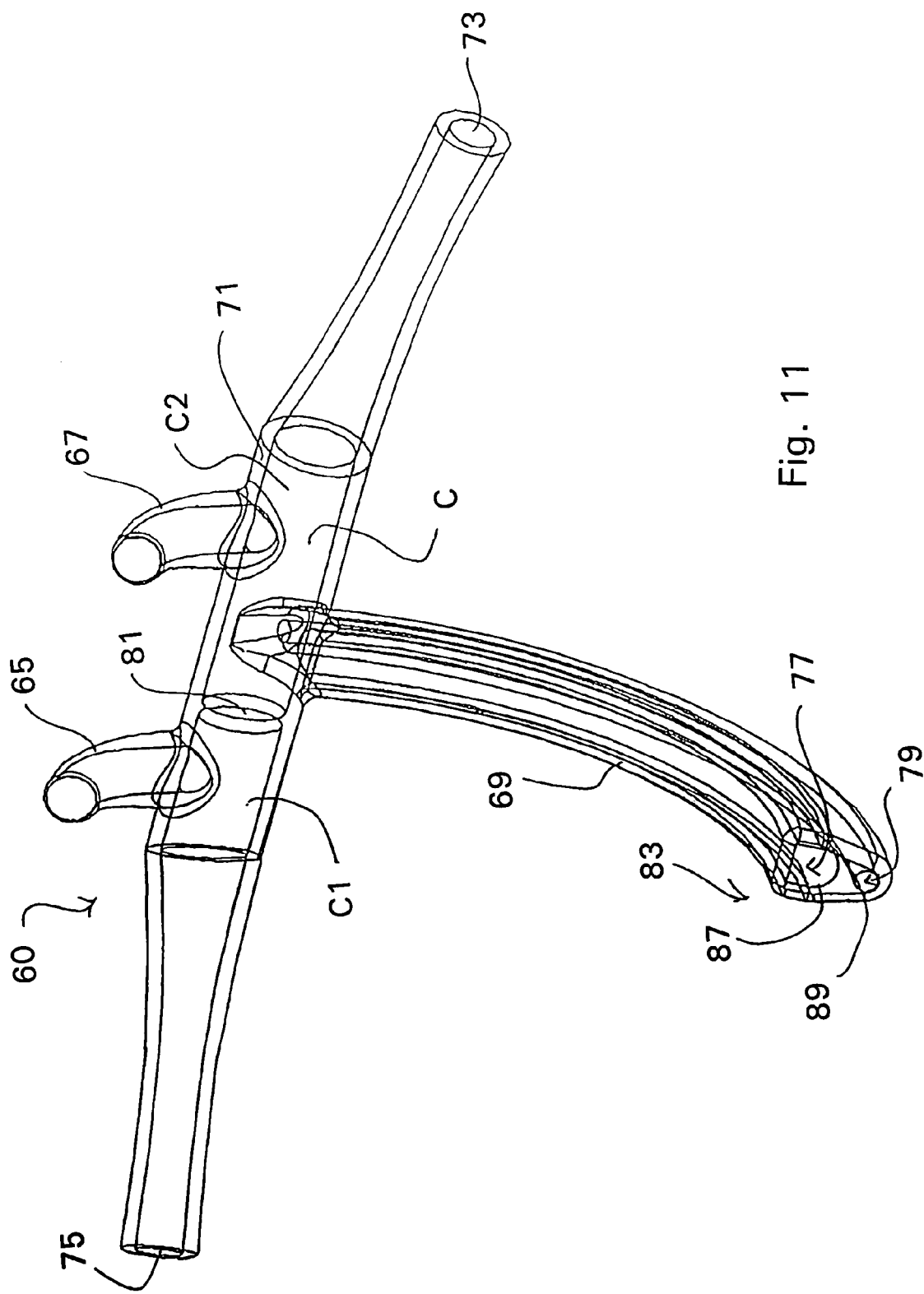
FIG. 11 is a perspective view of the cannula formed by the mandrel assembly and mouthpiece mandrel.

The manufactured cannula, formed by the above described cannula mandrel assembly and shown in FIG. 11, has a main body 71 with opposed internal chamber openings 73, 75 at either end of the main body 71 for coupling the opposed ends with flexible gas delivery, pressure detecting or gas sampling tubing or conduit, a pair of centrally located but spaced apart nasal prongs 65, 67 for insertion into the nostrils of a patient's nose, and a mouthpiece 69 located substantially at the middle of the main body 71, between the nasal prongs 65, 67. The mouthpiece 69 is connected to the main body and has a gas passageway 77 which communicates with the internal chamber C and a separate retainer lumen or passageway 79 formed therein for receiving the retaining or dead soft material. The septum 81 divides the internal chamber C into a first compartment or passageway C1 and a second separate compartment or passageway C2.

As best seen in FIG. 12A, the mouthpiece 69 of the nasal cannula 60 is shown with its originally molded shape which generally corresponds to the curvature of the mouthpiece mandrel 49. As can be appreciated, due to the nature of the resiliency of the plastisol material which forms the cannula 60, in the absence of any the retaining or dead soft material or any external biasing or motivating force or support, the mouthpiece 69 will generally retain and/or return back to this originally molded curvature. That is, if the mouthpiece 69 were configured into another orientation, the mouthpiece 69 will have a tendency to generally return or spring back to this originally molded curvature once the biasing force is removed or otherwise withdrawn.

Again observing FIG. 11, it is to be appreciated that the mouthpiece 69 is a unitary structure comprising the integrally formed passageway 79 for receiving the dead soft material or the shape retaining member, as well as the gas passageway 77. The mouthpiece 69 is connected with and maintains a gas flow path or communication between the gas passageway 77 and at least one compartment or passageway, e.g., C2, of the internal chamber C of the main body of the cannula and generally at least one nasal prong 67, assuming that the cannula 60 include an optional septum 81 which divides the internal chamber passageways C1 and C2, each compartment or passageway can facilitate preforming one of the following functions: monitor breathing of a patient, sampling the end tidal $CO_2$ content in the exhaled breath of a patient to determine the patient's $CO_2$ concentration level in the blood, or supplying a treating gas to a patient. In any event, the connection or coupling between the main body 71 and one end of the mouthpiece 69 includes the gas communication between the interior chamber C of the main body 71 and the gas passageway 77 in the mouthpiece 69, which is formed or created by the gas passage prong 53 of the mouthpiece mandrel 49.

Alternatively, it is to be appreciated that it is not necessary to have the mouthpiece 69 centered between the nasal prongs 65, 67. It is conceivable that the mouthpiece could be located on one side or the other of a central plane bisecting a center of main body 71 into two halves. Furthermore, it is also conceivable that a second gas passageway (not shown) which would permit a second function, e.g., monitor breathing of a patient, sampling the end tidal $CO_2$ content in the exhaled breath of a patient to determine the patient's $CO_2$ concentration level in the blood, or supplying a treating gas to a patient, could also be formed with the main body while the septum 81 remains generally centrally located within the main body of the cannula, e.g., coincident with the central plane bisecting the center of main body 71 into two halves. It is also to be appreciated that it is not necessary to have the septum 81 center within the main body as long as the septum 81 is generally located between the nasal prongs 65, 67. Also, as set forth in U.S. Pat. No. 6,439,234 to Curti et al., the disclosure of which is hereby incorporated by reference, additional openings, preferably adjacent the remote free end of each nasal prong, could be provided in the nasal prongs and possibly in the gas passageway of the mouthpiece to prevent occlusion of the prongs and facilitate monitoring, detecting, sampling, delivery, etc.

The passageway 79 for receiving the shape retaining member does not communicate with the interior chamber C of the main body 71. It is to be appreciated that due to the free end 63 of the retainer prong 55 of the mouthpiece mandrel being spaced from the connecting end 59 of the mouthpiece mandrel 49, a partitioning wall or barrier is formed therebetween by the plastisol material during the dipping process so that there is no communication between the bottom of the passageway 79, for receiving the shape retaining member, and either the gas flow passageway 77 and/or the internal chamber C of the main body 71 of the cannula 60, i.e., the passageway 79 is a blind passageway.

Now considering the unconnected or free end 83 of the mouthpiece 69, both the gas passageway 77 and the retainer passageway 79, for receiving the shape retaining member, terminate in respective and separate openings 87 and 89 which communicate with the external environment. Following manufacture of the cannula, the remote free end of the mouthpiece 69 is trimmed so that the mouthpiece 69 has a desired length. The gas passage opening 87 can provide the patient either with a treating gas, withdraw a sample of exhalation gas(es) from the patient, or monitor breathing characteristics, such as pressure, of the patient. With respect to the passageway 79, the retaining or dead soft material, as described above, is introduced through the passageway opening 89 and suitable secured within the retainer passageway 79 to permit desired adjustment or moldability of the mouthpiece 69, i.e., retention of a desired curvature, configuration and/or orientation of the mouthpiece 69 relative to a remainder of the cannula.

By way of example and now observing FIGS. 12A-C, a shape retaining member or dead soft material, in this case a length of copper wire 91 slightly shorter in length than the length of the retainer passageway 79, e.g., shorter by at least about 1/16 of an inch or so, can be pushed or inserted into the passage 79 so as to abut against a bottom of the blind passageway and secured therein by either a friction fit or by a suitable adhesive which does not interfere with or inhibit bending or movement of the wire 91 and/or mouthpiece 69. The wire 91 has a diameter and length which will readily be received within the retainer passageway 79, i.e., the wire 91 is completely received within the retainer passageway 79 so that one end of the wire abuts against or is located closely adjacent the bottom of the retainer passageway 79 while the opposite end of the wire 91 is located inside and spaced from the passageway opening 89 and thus does not protrude from or is directly exposed to the external environment. It is to be appreciated that the wire must be sufficiently long enough so as to provide the desired shape retention of the flexible mouthpiece 69, e.g., the wire should have a length which is at least 50% of the length of the retainer passageway 79, more preferably a length between about 60 to 98% of the length of the retainer passageway 79, most preferably a length between about 80 to 95% of the length of the retainer passageway 79. If desired, the wire 91 may be coated with an adhesive and then inserted in the retainer passageway 79. The adhesive then sets or cures to secure the wire 91 to the internal surface of the retainer passageway 79 and permanently retain the wire therein.

FIGS. 12A and 12B show a typical orientation of the mouthpiece 69 and the wire 91, relative to a the patient's mouth in the closed and opened positions, respectively, immediately following installation of the cannula on the patient but prior to any adjustment of the mouthpiece 69 and the wire 91, i.e., the mouthpiece 69 and the wire 91 exhibit their originally curvature. As can be readily observed in FIG. 12B, the gas passage opening 87 is generally not aligned with the exhalation/inhalation path E of the patient. The moldability and shape retention characteristics of the wire 91 allow the mouthpiece 69 to be adjusted or bent so that the gas passage opening 87 can be aligned with the exhalation/inhalation path E of the patient, as shown in FIG. 12C, and to appropriately retain and maintain this adjusted position or configuration of the mouthpiece 69. Such adjustable alignment and retention of the adjusted alignment, due to the retaining or dead soft material, permits both more accurate delivery of gas, enables more accurate sampling of the patient's exhaled gases, and facilitates more accurate monitoring of the patient's breathing. The above described arrangement permits bending, adjustment and/or reconfiguring of the mouthpiece 69, relative to a remainder of the cannula, into a desired shape, form or configuration while also ensuring that the adjusted or modified shape, form or configuration is retained and/or maintained.

As can be seen in FIG. 12A-12C, for example, the first end of the nasal prongs 65 and 67 generally form an angle of between about 110° to about 160°with the mouthpiece, preferably form an angle of about 130° or so.

A first modification to the mouthpiece mandrel 49 will now be discussed with reference to FIG. 13. As this embodiment is very similar to the embodiment of the mouthpiece mandrel 49 of FIG. 10, only the differences between this embodiment and the embodiment of FIG. 10 will be discussed in detail.

Figure 13:
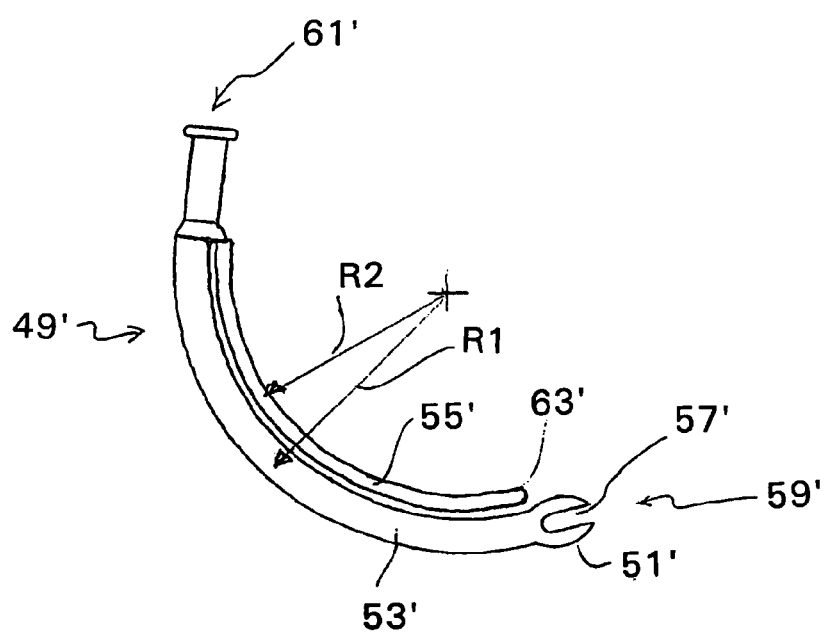
FIG. 13 is a front elevational view showing a modification to the mouthpiece mandrel in which the positions of the gas passage prong and the retainer prong are reversed.

The mouthpiece mandrel 49', as shown in FIG. 13, is fabricated so that the retainer prong 55' is located on the opposite side, from the location shown in FIGS. 10A-C, and is surrounded or encased by the gas passage prong 53', i.e., radius prong 55'. The radii of curvature R1 and R2 can vary but are generally chosen to facilitate the functional alignment of the cannula mouthpiece with a patient's open mouth. For example, these radii of curvature can range from between about 0.5 of an inch to about 2.5 inches or so, and more preferably can range from between about 0.75 of an inch to about 2.0 inches with radius R2 being slightly smaller than R1, e.g., smaller by ⅛ to ¼ of an inch or so. By this arrangement, the mouthpiece mandrel 49' defines a plane and both the retainer prong 55' and the gas passage prong 53' lie within that plane. One end of each of the gas passage prong 53' and the retainer prong 55' is structurally joined or fixedly connected with one another so that the retainer prong 55' is integral with and supported by the gas passage prong 53'. The mouthpiece mandrel 49', as shown in FIG. 13, attaches to the main body mandrel in the same manner discussed above, e.g., via engagement by a slot 57' formed in an end connector 51' at the connecting end 59' of the mouthpiece mandrel 49', as discussed above with respect to the embodiment of FIGS. 10A-C, for example.

A second modification to the mouthpiece mandrel 49 will now be discussed with reference to FIGS. 14A-C. As this embodiment is very similar to the embodiment of the mouthpiece mandrels 49 and 49' of FIGS. 10 and 13, only the differences between this embodiment and the embodiment of FIGS. 10 and 13 will be discussed in detail.

Figures 14A, 14B:
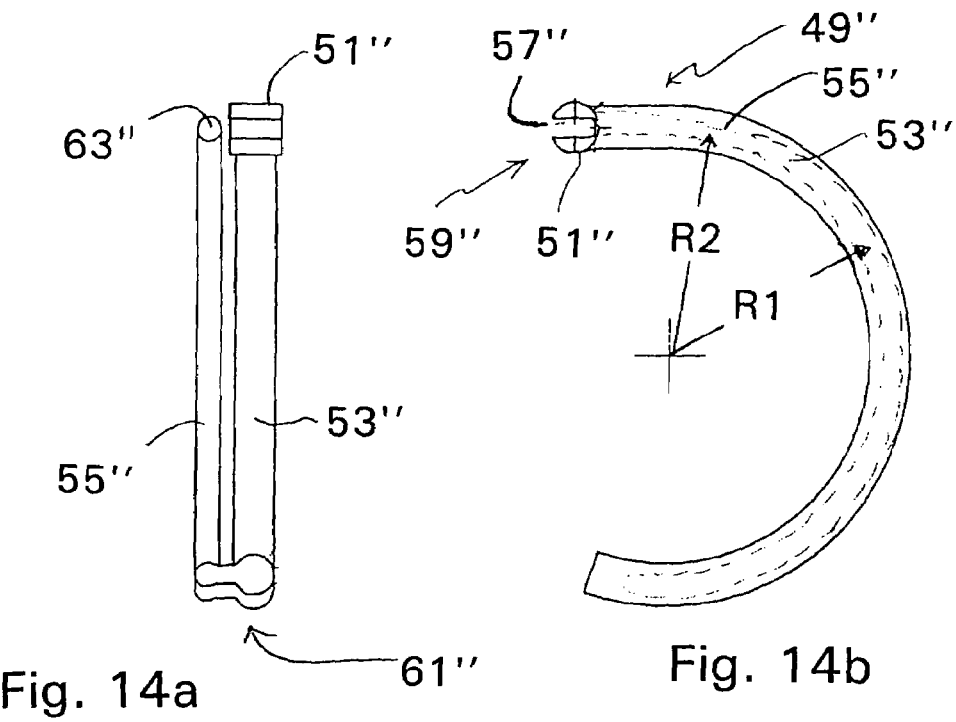
FIG. 14A is a front elevational view showing a modification to the mouthpiece mandrel.
FIG. 14B is diagrammatic side right elevational view of the mouthpiece mandrel of FIG. 14A.
Figures 14C, 14D:
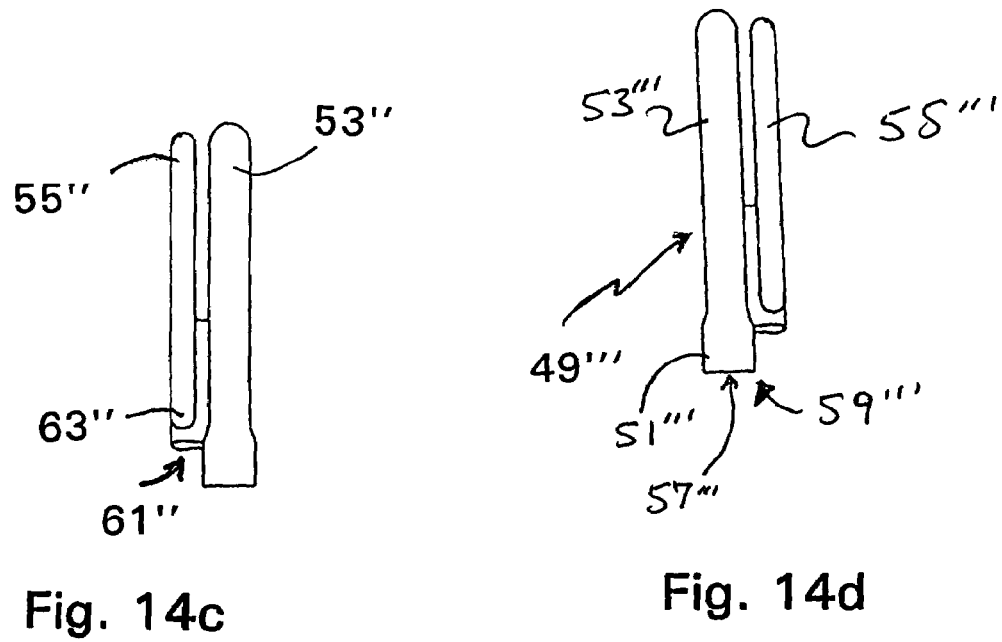
FIG. 14C is diagrammatic top elevational view of the mouthpiece mandrel of FIG. 14A.
FIG. 14D is a diagrammatic top elevational view, similar to FIG. 14C, showing a further modification to the mouthpiece mandrel in which the retainer prong is located on the opposite side of the gas passage prong.

The mouthpiece mandrel 49", as shown in FIGS. 14A-C, is fabricated so that the retainer prong 55" is located along side and extends side by side and parallel to the gas passage prong 53" of the mouthpiece mandrel 49", i.e., radius R1 of the gas passage prong 53" is substantially identical to the radius R2 of the retainer prong 55", as can be seen in FIG. 14B. That is, the retainer prong 55" defines and lies within a first plane and the gas passage prong 53" defines and lies within another plane located closely adjacent to but spaced from and extending parallel to the plane defined by the retainer prong. One end of the retainer prong 55" is structurally joined or fixedly connected with an adjacent end of the gas passage prong 53" so that the retainer prong 55" is integral with and supported by the gas passage prong 53". The mouthpiece mandrel 49", as shown in FIGS. 14A-C, attaches to the main body mandrel in the same manner discussed above, e.g., via engagement by a slot 57" formed in an end connector 51" at the connecting end 59" of the mouthpiece mandrel 49", as discussed above in further detail with respect to the embodiment of FIGS. 10A-C, for example.

A still further modification to the mouthpiece mandrel 49 will now be discussed with reference to FIG. 14D. As this embodiment is very similar to the embodiment of the mouthpiece mandrels 49 and 49', 49" of FIGS. 10, 13 and 14A-C, and in particular the embodiment of FIGS. 14A-14C, only the differences between this embodiment and the embodiments of FIGS. 10, 13 and 14A-C will be discussed in detail.

The mouthpiece mandrel 49''', as shown in FIG. 14D, is fabricated so that the retainer prong 55''' is located along side and arranged parallel to the gas passage prong 53''' of the mouthpiece mandrel 49''', i.e., radius of the gas passage prong 53''' is substantially identical to the radius of the retainer prong 55'''. That is, the retainer prong 55''' defines and lies within a plane and the gas passage prong 53''' defines and lies within another plane located closely adjacent to but spaced from and extending parallel to the plane defined by the retainer prong. One end of the retainer prong 55''' is structurally joined or fixedly connected with an adjacent end of the gas passage prong 53" so that the retainer prong 55''' is integral with and supported by the gas passage prong 53'''. The mouthpiece mandrel 49''', as shown in FIG. 14D, attaches to the main body mandrel in the same manner discussed above, e.g., via engagement by a slot 57''' formed in an end connector 51''' at the connecting end 59''' of the mouthpiece mandrel 49''', as discussed above in further detail with respect to the embodiment of FIGS. 10A-C, for example.

It is to be appreciated that the retainer prong may be positioned at any desired location about the circumference of the gas passage prong such that the retainer prong is aligned and extends substantially side by side and parallel to gas passage prong. The arrangements of FIGS. 14A-C and 14D are preferred as they facilitate adjustment of the position, configuration and/or orientation of the gas passageway 77 with respect to a remainder of the cannula while minimizing the possibility of kinking of the gas passageway 77.

With reference to FIGS. 15A-G, a still further embodiment of the present invention is shown which comprises a mouthpiece mandrel stub 149, instead of a mouthpiece mandrel having both a gas flow prong and a retainer prong. It is to be appreciated that due to manufacturing constraints and associated time and expense, it may be more difficult to produce the cannula with an integral mouthpiece during a single manufacturing step or process. Accordingly, it may be beneficial to produce the cannula as two separate components which are subsequently integrally joined or connected with one another. For example, the cannula main body or facepiece can be manufactured by a dipping process while a mouthpiece may be extruded or otherwise fabricated, during a completely separate manufacturing process, and subsequently attached or otherwise permanently secured to the cannula facepiece as described below.

Figure 15A:
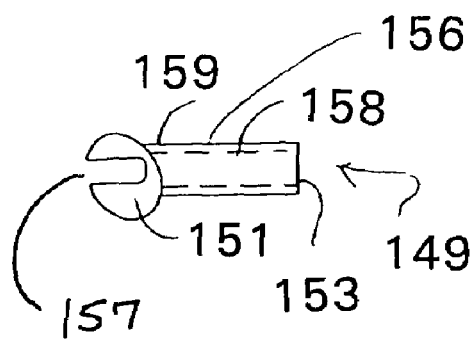
FIG. 15A is a diagrammatic side elevational view of a mandril stub.
Figure 15B:
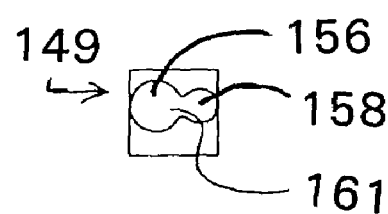
FIG. 15B is a diagrammatic right end view of the mandril stub taken along section 15B-15B of FIG. 15A.
Figure 15C:
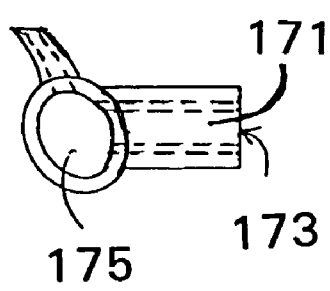
FIG. 15C is a diagrammatic transverse cross sectional view of a cannula manufactured by the mandril stub of FIGS. 15A and 15B.
Figure 15D:
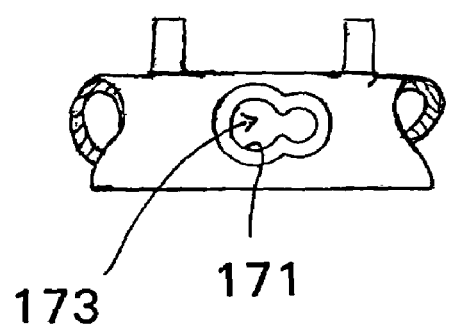
FIG. 15D is a diagrammatic fragmented front elevational view of the facepiece of a cannula, taken along section line 15D-15D of FIG. 15C, showing the formed receiving opening.

The mouthpiece mandrel stub 149 comprises an end connector 151 and a relatively short extension portion 153, i.e., no retainer prong or gas passage prong is provided thereon. An optional neck section 159, possibly having a reduced cross sectional area, may connect the mouthpiece mandrel stub 149 with the extension portion 153. The extension portion 153 is formed by a pair of adjacent and conjoined solid cylindrical members 156, 158 which project from the end connector 151 a sufficient length, for example, a length of about 1/16 of an inch to about 1/4 of an inch or so, to facilitate subsequent connection of a separate mouthpiece, as discussed below in further detail. The extension portion 153 terminates in an end surface 161. The end surface 161, as can be seen in FIG. 15B, generally has a "snowman" transverse cross section or profile. The conjoined solid cylindrical members 156, 158 typically have a diameter of from about 1/16 of an inch to about 3/8 of an inch or so. The neck section 159 typically has a diameter of about of about 1/32 of an inch to about 1/4 of an inch or so and a length of about 1/64 of an inch to about 1/4 of an inch or so.

During assembly of the cannula mandrel assembly, as with the embodiment of FIG. 2, the slot 157 of the mouthpiece mandrel stub 149 is sized to permit close contact and engagement with the rectangular section 21 of main body mandrel such that a snug fit or attachment is obtained so as to removably retain the mouthpiece mandrel stub 149 engaged with the main body mandrel during dipping while still facilitating extraction of the mouthpiece mandrel stub 149 from the rectangular section 21 following at least partial curing of the PVC, or some other plastisol or plastics material, on the cannula mandrel assembly. The outer surface of the end connector 151 is sized to approximate a continuation of the outer surface or diameter of the main body mandrel to provide a substantially uniform amount of applied PVC, or some other plastisol or plastics material, to the cannula mandrel assembly while still facilitate withdrawal of mouthpiece mandrel stub 149 from both a remainder of the cannula mandrel assembly and a receiving opening 173 formed in the facepiece of the cannula, discussed below in further detail.

In the event that the main body forming mandrel is formed as two components, namely, first and second slightly spaced apart components (not shown) which remain spaced apart from one another by a small gap or void following assembly of the cannula mandrel assembly 3 as well as during the dipping process or operation. The small gap or void becomes, during the dipping process, filled with PVC, or some other plastisol or plastics material, and forms a septum which forms a partition or barrier within the main body thereby dividing the internal chamber of the cannula into two separate compartments or passageways. In the event that the main body forming mandrel is formed as a single continuous mandrel component, without any gap or void therein, the internal chamber of the cannula is formed as a single interior compartment or passageway, i.e., an undivided cannula.

Following dipping and sufficient curing of the plastisol on the cannula mandrel assembly, including the mouthpiece mandrel stub 149 and the extension portion 153, a portion of the cured plastisol extending adjacent to and along the end surface 161 of the extension 153 is cut away or otherwise removed to form the receiving opening 173 and expose the end surface 161 of the mandrel stub 149 and permit removal of the entire mandrel stub 149 from the cured plastisol and a remainder of the cannula mandrel assembly out through the receiving opening 173. Once the mandrel stub 149 is removed, the space previously occupied by the extension portion 153 forms a receiving passage 171 which has a "snowman" transverse cross section or profile which closely corresponds to the "snowman" transverse cross section or profile of the removed extension portion 153. An opposed end of the receiving passage 171, remote from the receiving opening 173, directly communicates with the one of the internal compartments C1 or C2 of the divided cannula via an aperture formed by the connecting end 151 and/or neck of the mandrel stub 149 once the mandrel stub 149 is removed from the remainder of the cannula mandrel assembly. The cured plastisol, which adheres to the exterior surface of the extension portion 153 of the mandrel stub 149, forms a receiving housing 172 which typically has a wall thickness of between 1/32 and 3/8 of an inch, preferably about 1/8 of an inch or so.

The receiving passage 171 and the receiving passage 173, formed in the nasal facepiece of the cannula, facilitate attachment or otherwise permanently affixing or securing of a separate mouthpiece 181 to the nasal facepiece of the cannula, as discussed below in further detail. A two step manufacturing process may be beneficial in reducing manufacturing problems which may be associated with forming the entire nasal cannula during a single step manufacturing process. A two step manufacturing technique simplifies the manufacturing process by eliminating the difficulty in attempting to extract the long mandrel prongs from the cured plastisol without damaging the cannula.

Although the receiving opening 173 and the receiving passage 171 are shown as generally having a "snowman" transverse cross section or profile, it is to be appreciated that the receiving opening 173 and the receiving passage 171 can have a variety of different shapes, sizes, diameters, configurations, profiles, cross sections, etc. The important criteria is that the interior profile and/or shape of the receiving opening 173 and the receiving passage 171 closely mirror or correspond to the exterior profile and/or shape of the separate mouthpiece 181 so that those surfaces can intimately mate and form a gas impermeable seal with one another.

The separate mouthpiece 181, which is inserted into the receiving opening 173, may be formed by a separate extrusion process, or some other known or conventional manufacturing technique or process. Following manufacture of the cannula and removal of the mandrel stub 149, the separate mouthpiece 181 is then inserted or pushed in though the receiving opening 173 so as to partially fill the receiving passage 171. Although it is possible to retain the separate mouthpiece 181 within the receiving opening 173 merely by a frictional fit, generally glue or some other conventional fastener, e.g., MEK, is utilized to secure or otherwise permanently attach or affix the separate mouthpiece 181 therein.

The mouthpiece 181, shown in FIGS. 15E, 15F and 15G, comprises a pair of adjacent and interconnected flexible tubes or conduits 183 and 185, e.g., a flexible retainer tube or conduit 183 and a flexible gas flow tube or conduit 185 which define respectively therein an internal retainer passageway 193 and a gas flow passageway 195. According to FIG. 15G, the gas flow passageway 195 has a larger internal transverse cross sectional area than the internal transverse cross sectional area of the retainer passageway 193. The dead soft material, having a corresponding shape and/or size, is inserted within the retainer passageway 193. The internal transverse cross sectional area of the gas flow passage 195 is selected so as to facilitate desired gas flow in either flow direction, e.g., for delivery, sampling, detecting, etc., of desired quantity of gas(es). Accordingly, the shape and/or size of the gas flow passageway 195, the retainer passageway 193, the flexible retainer tube or conduit 183 and the flexible gas flow tube or conduit 185 can vary depending upon the particular application. For example, the retainer passageway 193 may be smaller, larger or the same size as the gas flow passageway 195.

Figure 8:
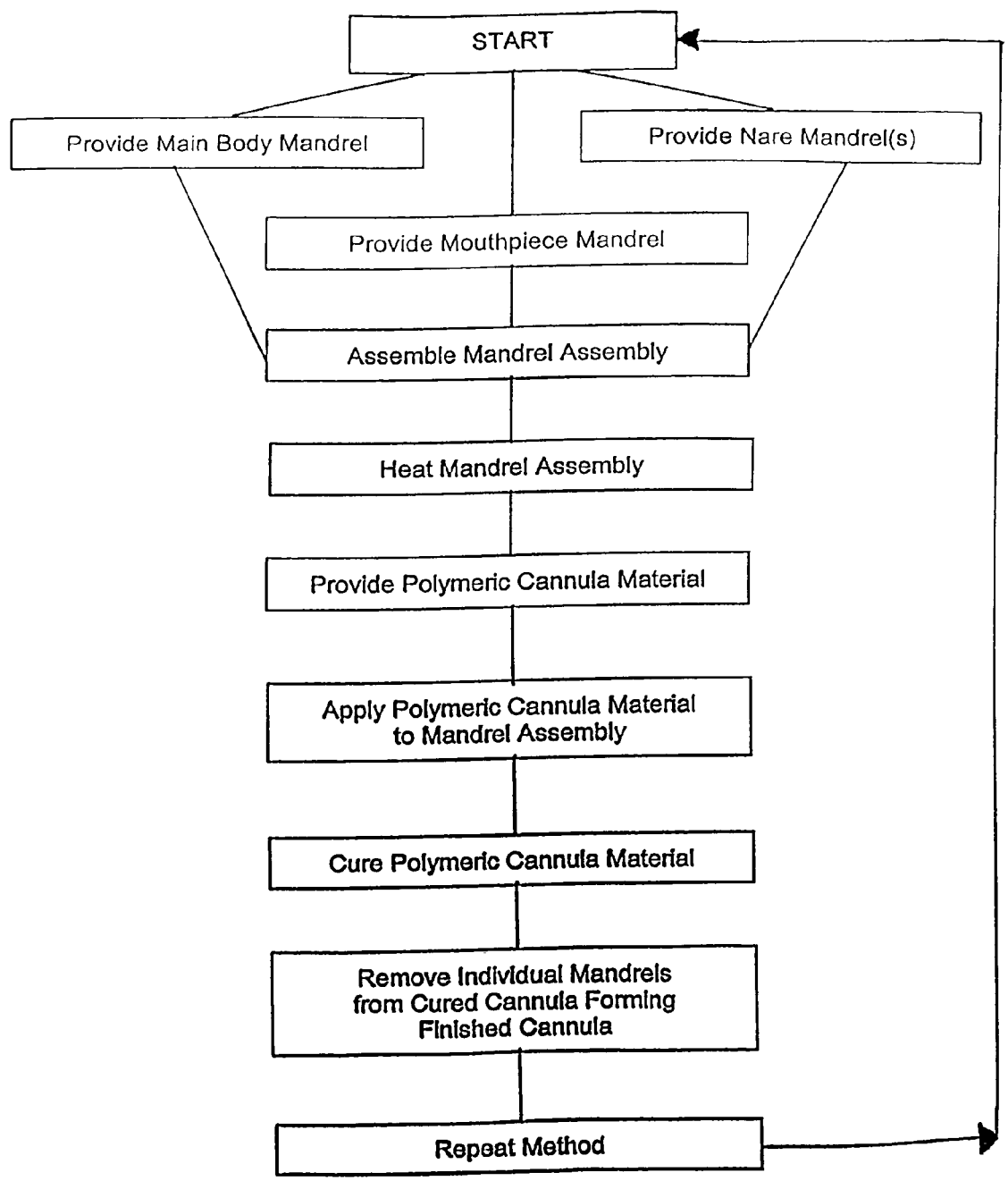
FIG. 8 is a flow diagram of the method of the present invention.
Figure 9:
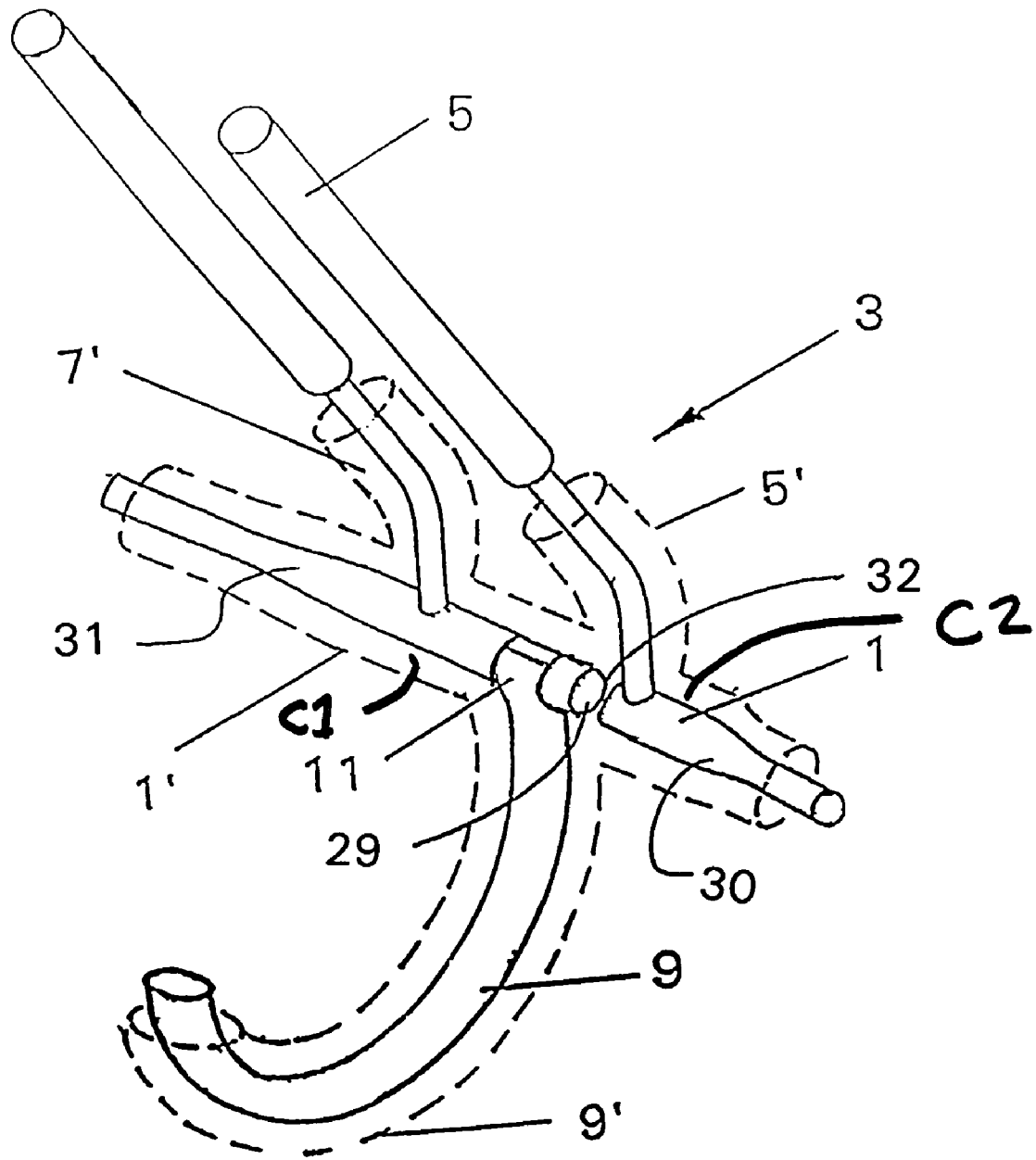
FIG. 9 is an orthogonal view of a cannula mandrel assembly for forming a septum or barrier in a void of the main body forming mandrel, with cannula forming polymeric material shown in ghost.

The flexible retainer tube or conduit 183 and the flexible gas flow tube or conduit 185 are formed or joined with one another along a common elongate side surface to a form mouthpiece generally having a "snowman" or "FIG. 8" profile, as shown in FIG. 15G. It is to be appreciated that the outer surfaces of these adjacent tubes could be of any particular shape and/or configuration, however, for ease of manufacture and purposes of description, the outer surfaces of the respective tubes are shown substantially cylindrical and joined along an elongate length thereof to form the FIG. 8 profile.

To complete manufacture of the cannula, a leading end of a desired length of the separate mouthpiece 181 is snugly inserted, i.e., via a friction fit or by an adhesive such as MEK, within the receiving passage 171. The free end of the mouthpiece 181 thus defines a retainer receiving opening 197 and a gas flow opening 199 for positioning near a patient's mouth. As can be readily appreciated, a long extruded length of the mouthpiece can be manufactured and thereafter cut into a desired number of smaller lengths to form a plurality of separate mouthpiece extensions 181 so that each mouthpiece 181 can be attached to a nasal cannula relatively inexpensively. The dead soft material may be inserted into the retainer passageway 193 of the mouthpiece extension(s) 181 at any point during the manufacturing process, either during manufacture of the long extruded length of the mouthpiece or before or after attachment of the mouthpiece 181 to the cannula.

Depending upon the relative positioning of the extension portion 153 with respect to a remainder of the mouthpiece mandrel stub 149, the relative position of the retainer passageway 193 with the gas flow passageway 195 can be easily altered or modified so that the retainer passageway 193 can be situated anywhere about the 360° circumference of the gas flow passageway 195. That is, the retainer passageway 193 could be on either the left side of the gas flow passage 195, as shown in FIGS. 15E-15G, or could be position on the opposite side (not shown), etc. Preferably, however, the retainer passageway 193 and the gas flow passageway 195 are formed side by side and extend parallel to one another as shown in FIG. 15F, for example.

With reference to FIGS. 16-18B, a further variation of the method for manufacturing the cannula as well as the cannula manufactured therefrom will now be described. According to this embodiment, the mouthpiece mandrel stub 149 comprises a pair of spaced apart end connectors 251 and a relatively short extension portion 253, i.e., no retainer prong or gas passage prong is provided on the mandrel stub. An optional neck section 259, typically of a reduced cross sectional area, may interconnect each associated end connector 251 with the extension portion 253. The extension portion 253 is formed by three serially aligned, adjacent and conjoined solid cylindrical members 256, 258, 262 which project from the end connector 251 a sufficient length, for example, a length of about 1/16 of an inch to about 1/4 of an inch or so, to facilitate subsequent connection of the separate mouthpiece 281. The extension portion 253 terminates in an end surface 261. The end surface 261, as can be seen in FIG. 16B, generally has a "three section snowman" transverse cross section or profile, e.g., two smaller outer solid cylindrical members 256 and 262 and a larger central solid cylindrical member 258. The conjoined solid cylindrical members 256, 258, 262 typically have a diameter of from about 1/16 of an inch to about 3/8 of an inch or so. Each neck section 259 typically has a diameter of about of about 1/32 of an inch to about 1/4 of an inch or so and a length of about 1/64 of an inch to about 1/4 of an inch or so.

During fabrication of the cannula mandrel assembly, as with the previous embodiments, the slot 257 of a first one of the end connectors 251 is sized to permit close contact and engagement with a mating rectangular section 260 of one of the two components which together form the main body mandrel. Similarly, the slot 257 of the second one of the end connectors 251 is also sized to permit close contact with a mating rectangular section 260 of the other one of the two components which together form the main body mandrel. Both slots 257 have a snug fit or attachment with the mating rectangular sections 260 so as to facilitate retaining the mouthpiece mandrel stub 249 engaged with the main body mandrel while still facilitating extraction of the mouthpiece mandrel stub 249 from both of the mating rectangular sections 260 following at least partial curing of the PVC, or some other plastisol or plastics material, on the cannula mandrel assembly. As with the previous embodiments, the outer surface of the end connector 251 is sized to approximate a continuation of the outer surface or diameter of the main body mandrel to provide a substantially uniform amount of applied PVC, or some other plastisol or plastics material, to the cannula mandrel assembly while still facilitate withdrawal of mouthpiece mandrel stub 149 from both the cannula mandrel assembly and the receiving passage 271, as discussed below.

The two components, forming the main body forming mandrel, are spaced apart from one another by a small gap or void 232, e.g., a distance of between about 1/32 of and inch to about 1/4 of an inch or so. The small gap or void 232, during the dipping process, becomes filled with PVC, or some other plastisol or plastics material, and forms the septum 281 (see FIGS. 17A and 17B) which forms a partition or barrier within the main body thereby dividing the internal chamber C of the cannula into two separate compartments or passageways C1 and C2. In the event that the main body forming mandrel is formed as a single continuous component without any gap or void therein, the internal chamber C of the cannula is not divided, i.e., it is formed as a single unitary interior compartment or passageway. The mandrel extension 253, as seen in FIG. 16B, has a cross section designed to form a receiving passage 271 and receiving opening 273 in a side surface of the facepiece of the cannula which facilitates insertion and attachment of the mouthpiece 281. In the disclosed embodiment, the mandrel extension 253 cross section has a multi-cylindrical outer profile which closely corresponds to the multi-cylindrical outer profile of the triple lumen or triple tube mouthpiece extension 281.

To form the cannula assembly, as shown in FIG. 16C, the pair of connecting ends 251 of the mandrel snub 249 are each respectively connected with one of the respective rectangular portions 260 of the respective main body mandrels 250, 252 and thereby form an internal T-shaped area between the main body mandrel, the pair of connecting ends 251 and the mandrel extension 253, as seen in FIG. 16C. The mandrel 249 is now ready to be dipped into the liquid plastisol.

Figure 17A:
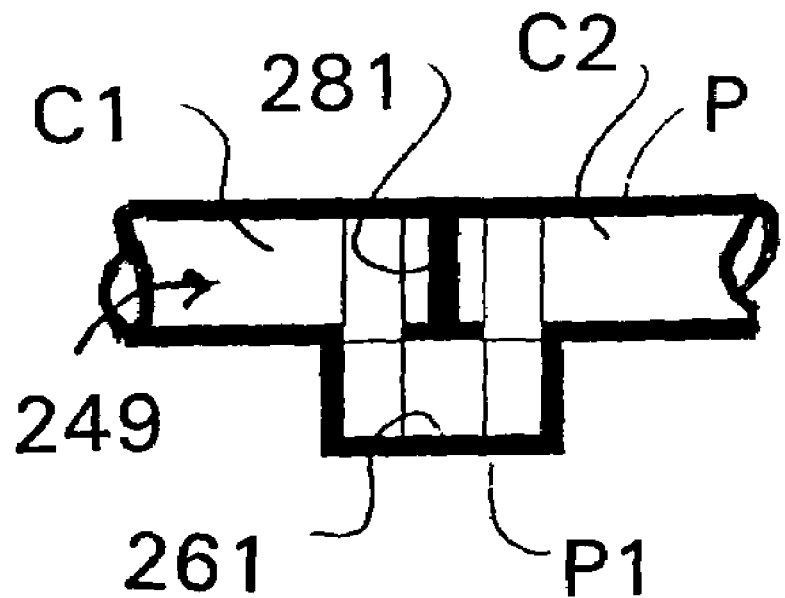
FIG. 17A is a diagrammatic transverse cross sectional front of a facepiece manufactured from the mandrel assembly of FIG. 16C.
Figure 17B:
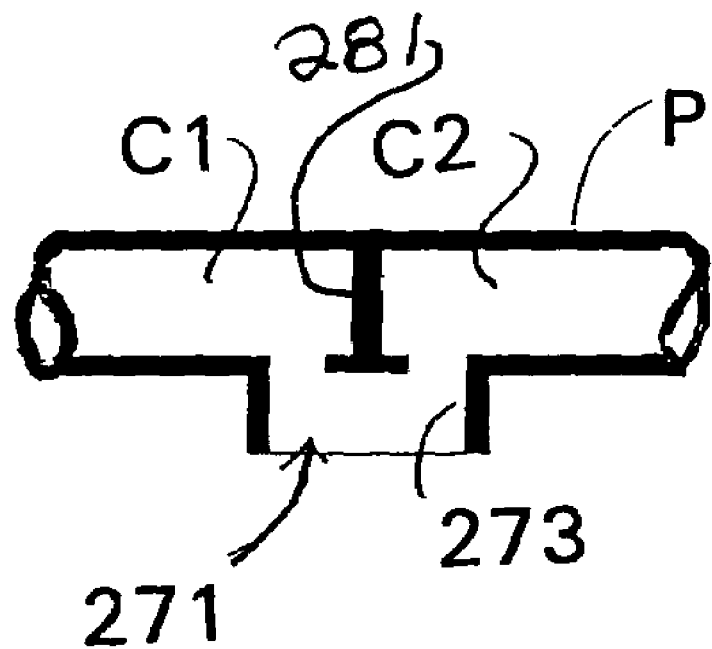
FIG. 17B is a diagrammatic transverse cross sectional view, similar to FIG. 17A, one the end surface of the facepiece is removed and following extraction of the mandrel stub through the receiving opening.

After the mandrel stub 249 is connected with the main body mandrels 250, 252 and dipped into a plastisol material and then subsequently cured, the mandrel 249 is coated with a uniform layer of plastisol P as shown in FIG. 17A, including filling the T-shaped area of the mandrel which forms a partition or septum 281 dividing the cannula into two separate compartments or passageways C1 and C2. In order to disassemble and remove the mandrel 249 from the cannula, a layer of plastisol P1, covering and extending along the end surface 261 of the extension 253, is cut away or removed to form a receiving opening 273 which provides access to the mandrel stub 249 so that the mandrel stub 249 can thereafter be disengaged and removed from the main mandrel sections 250, 252 and pulled out of the cannula through the receiving opening 273. The two main mandrel section 250, 252 are then also free to be removed laterally through the opposed ends of the cannula, as discussed above. Thus, the receiving opening 273 is created for providing communication with the receiving passage 271 for subsequent attachment of the mouthpiece 281.

Once the mandrel stub 249 is removed, the space previously occupied by the extension portion 253 forms a receiving passage 271 having a "three section snowman" or triple lumen transverse cross section or profile which intimately corresponds to the "three section snowman" or triple lumen transverse cross section or profile of the extension portion 253. Such removal also facilitates formation of two spaced apart flow apertures establishing communication between each one of the internal compartments C1 and C2 of the internal chamber C with the receiving passage 271. The two spaced apart flow apertures are generally formed by the neck sections 259 and/or the corresponding end connectors 251. The cured plastisol, which adheres to the exterior surface of the extension portion 253 of the mandrel stub 249, typically has a wall thickness of between 1/32 and 3/8 of an inch, preferably about 1/8 of an inch or so.

The receiving opening 273, formed in the nasal facepiece of the cannula, facilitates attachment or otherwise permanently affixing or securing a separate mouthpiece 281 to the nasal facepiece of the cannula which may be manufactured by a separate manufacturing process.

Although the receiving passage 271 and the receiving opening 273 are shown as generally having a "three section snowman" or triple lumen transverse cross section or profile, it is to be appreciated that they can have a variety of different shapes, sizes, diameters, configurations, profiles, cross sections, etc. The important criteria is that the interior profile or shape of both the receiving passage 271 and the receiving opening 273 closely mirror or correspond to the exterior profile or shape of the separate mouthpiece 281 so that those surfaces can intimately mate and form a gas impermeable seal with one another.

The separate mouthpiece 281, which is inserted into receiving opening 273, may be formed by a separate extrusion process, or any other known or conventional manufacturing technique or process. Following manufacture of the cannula and removal of the mandrel stub 249, the separate mouthpiece 281 is inserted or pushed into the receiving opening 273 to fill the receiving passage 271. The top of the T-shaped area as well as a remainder of the bottom of the receiving opening 273 forms a stop surface which prevents further insertion movement of the separate mouthpiece 281 into the receiving passage 271. Although it is possible to retain the separate mouthpiece 281 within the attachment opening 273 merely by a frictional fit, general glue or some other conventional fastener, e.g., MEK, is utilized to secure or otherwise permanently attach the separate mouthpiece 281 therein.

The mouthpiece 281, shown in FIGS. 18A and 18B, comprises a three serially aligned, adjacent and interconnected flexible tubes or conduits 283, 285 and 287 which each respectively define therein a first gas flow passageway 291, a central retainer passageway 293 and a second gas flow passageway 295. As can be seen in FIG. 18B, the outer diameter of the centrally located tube or conduit is larger in size than the outer diameter of either of the two end conduits or tubes and the central retainer passageway 293 has a larger internal transverse cross sectional area than the internal transverse cross sectional area of both the first and second gas flow passageways 291 and 295. Typically a small diameter dead soft material, such as copper wire for example, is provided for adequate adjustment of the mouthpiece and thus the retainer passageway 293 is correspondingly sized to receive a desired dead soft material. The transverse cross sectional areas of the first and second gas flow passageways 291 and 295 are selected so as to facilitate adequate gas flow of a desired quantity of gas there along, in either flow direction, to facilitate delivery, monitoring, detecting, sampling, etc. Accordingly, the shape and/or size of the flexible tubes or conduits 283, 285 and 287, the first and second gas flow passageways 291 and 295, and the retainer passageway 293 can vary depending upon the particular application. For example, the retainer passageway 293 could be either smaller or the same size as one or both of the first and second gas flow passageways 291 and 295.

The flexible gas flow tube or conduit 283 is formed or joined with the flexible retainer tube or conduit 285 along a common side surface while an opposite side surface of the flexible retainer tube or conduit 285 is formed or joined with the flexible gas flow tube or conduit 287 to form a mouthpiece generally having a "three section snowman" or triple lumen configuration or profile, as shown in FIG. 18B. It is to be appreciated that the outer surfaces of these adjacent tubes or conduits 283, 285 and 287 can be of any desired shape or configuration depending upon the particular application.

To complete assembly of a completed cannula, a leading end of a desired length of the separate mouthpiece 281 is snugly inserted, i.e., via a friction fit or by an adhesive such as MEK, for example, within the receiving passage 271. The remote free end of the mouthpiece 281 thus defines a retainer receiving opening 297 and a pair of spaced apart gas flow openings 299 and 301 which may be adjusted or positioned, during use, near a patient's mouth. The dead soft material, e.g., copper wire, may be inserted into the retainer passageway 293 at any point during the manufacturing process, e.g., either during manufacture of the separate mouthpiece 281 or before or after attachment of the separate mouthpiece 281 to the facepiece of the cannula.

Depending upon the relative positioning of the extension portion 253 with respect to a remainder of the mouthpiece mandrel stub 249, the relative position of the flexible gas flow tubes or conduits 283 and 287 with respect to the flexible retainer tube or conduit 285 can be easily altered or modified so that the flexible gas flow tubes or conduits 283 and 287 can be situated anywhere about the 360° circumference of the flexible retainer tube or conduit 285. Preferably, however, the flexible retainer tube or conduit 285 is centrally located between both of the flexible flow tubes or conduits 283 and 287 as shown in FIGS. 18A and 18B.

Figure 19C:
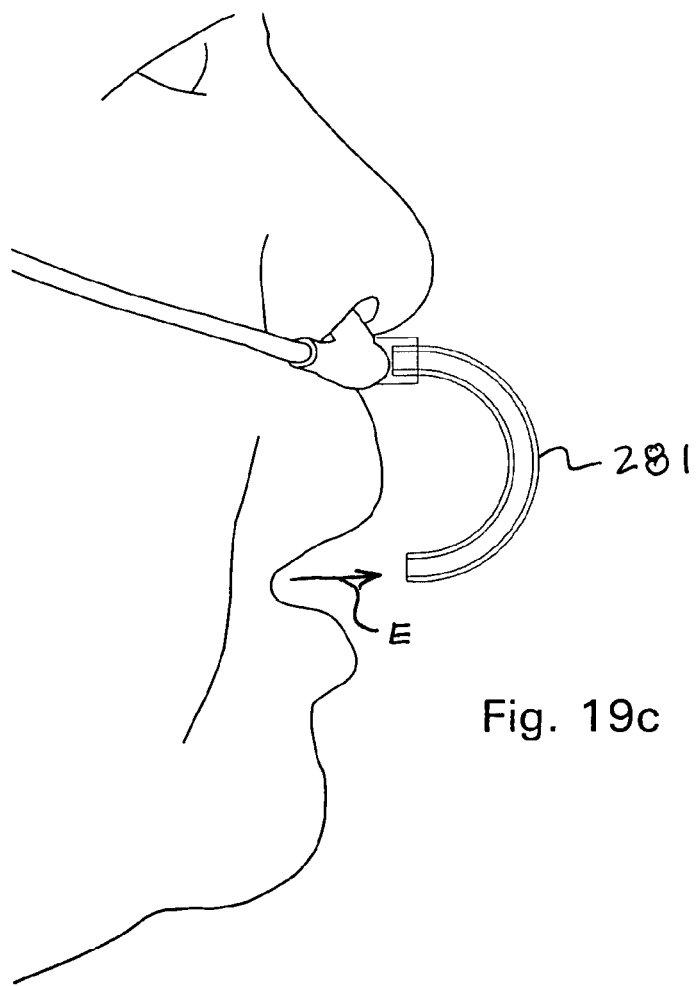
FIG. 19C is a diagrammatic side elevational view showing the proper orientation of the mouthpiece of FIGS. 19A and 19B relative to the open mouth of the patient.
Figure 19B:
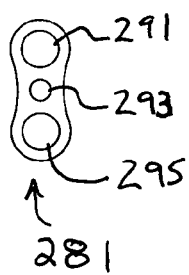
FIG. 19B is a diagrammatic left end view of the separate mouthpiece of FIG. 19A.
Figure 19A:
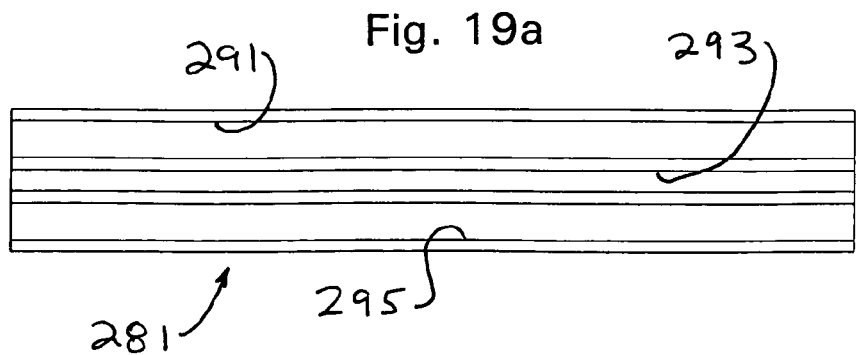
FIG. 19A is a diagrammatic front elevational view showing a variation of the separate mouthpiece.

As shown in FIGS. 19A-19C, a variation of the extruded mouthpiece 281 is shown. According to this embodiment, the mouthpiece is also a triple lumen, however, the centrally located retainer passage 293 has a transverse cross-sectional area which is smaller in size than both the first and second gas flow passageways 291 and 295. Although not shown, the facepiece will have a correspondingly shaped receiving passage and receiving open which closely mirror and/or correspond to the exterior profile of the separate mouthpiece 281 so those surfaces can intimately mate and form a gas impermeable seal with one another. With reference to FIG. 19C, a two-piece cannula, manufactured from the mouthpiece 281 of FIGS. 19A and 19B, is shown with the opening of the mouthpiece located so as to be aligned with the exhalation/inhalation path E of the patient.

Figure 20:
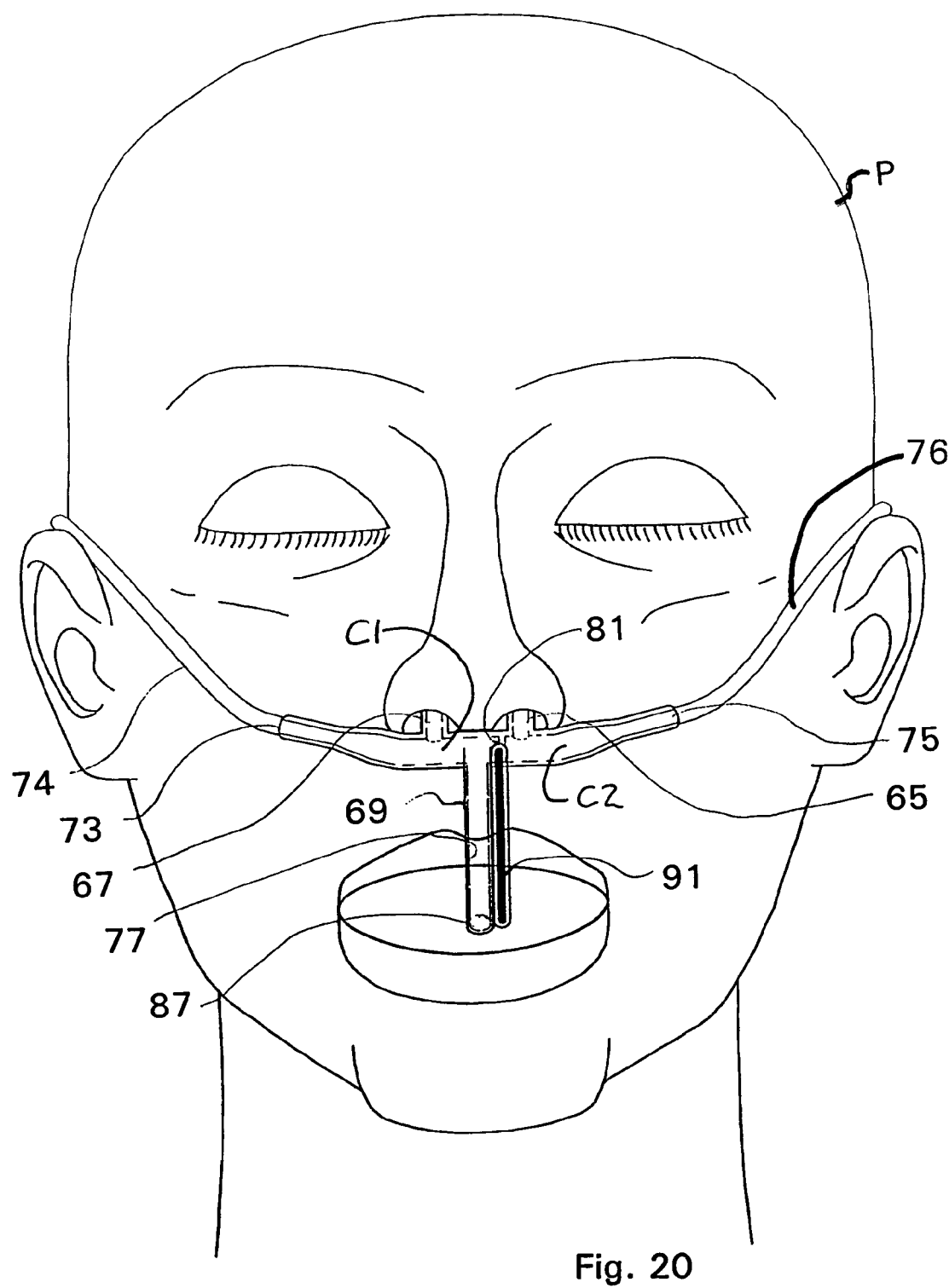
FIG. 20 is a diagrammatic front elevational view showing the proper orientation of the mouthpiece of a cannula relative to an open mouth of the patient.
Figure 21:
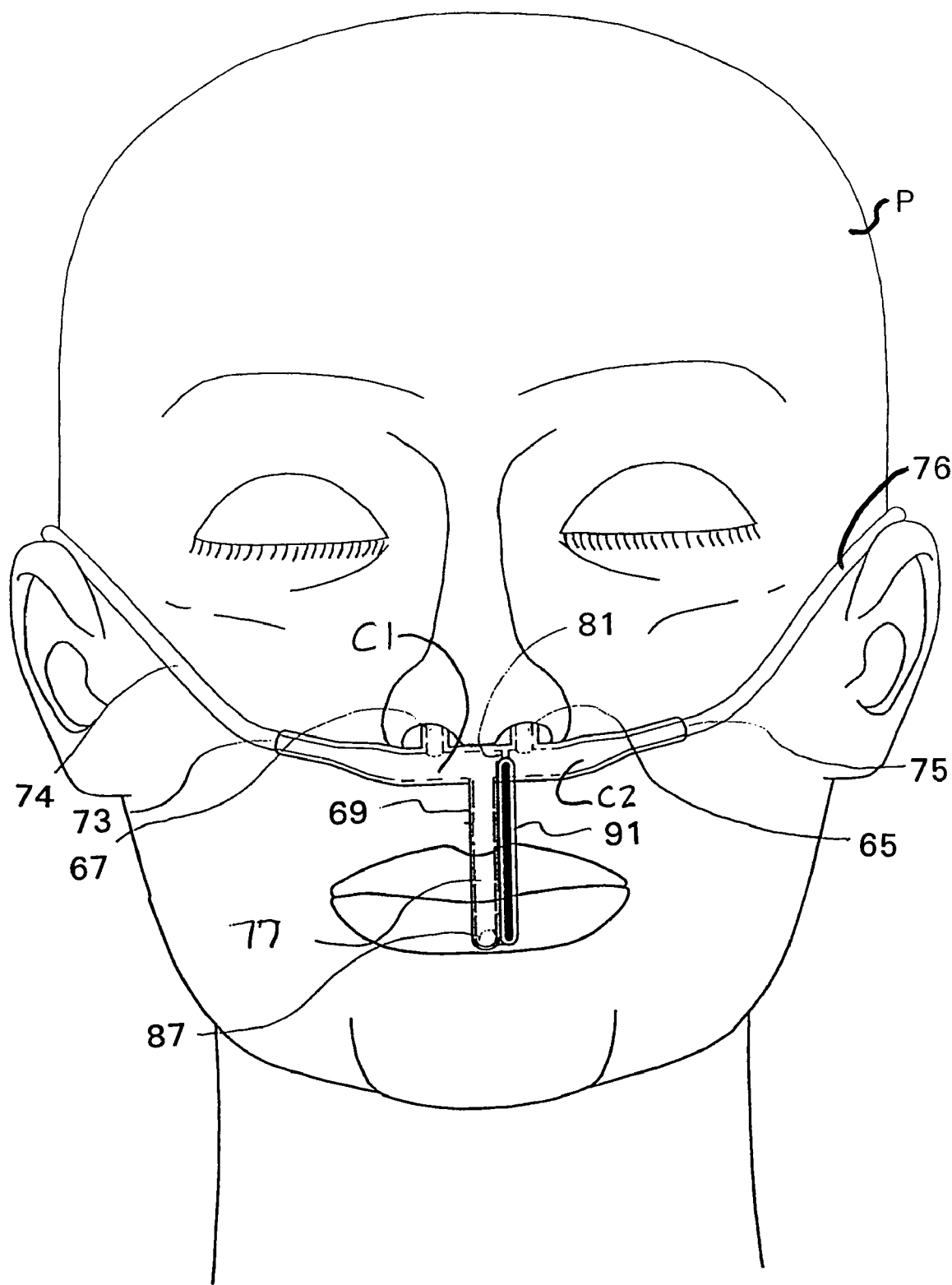
FIG. 21 is a diagrammatic front elevational view, similar to FIG. 20, showing the proper orientation of the mouthpiece of a cannula relative to a closed mouth of the patient.

With reference now to FIGS. 20 and 21, a typical positioning or setting up for the cannula with the nostrils and the mouth of patient are shown. The only difference between FIGS. 20 and 21 is that FIG. 20 shows the proper installation of the cannula with the patient's mouth open while FIG. 21 shows the same positioning or location of the cannula with the patient's mouth closed. As can be seen in both of these Figures, each of the nasal prongs 65, 67 is located or accommodated within a respective one of the nostrils (not numbered) of the patient while the gas passage opening 87 is aligned to communicate with the patient's exhalation/inhalation path E so that the exhalation breath of the patient can readily enter into the gas passageway opening 87 and flow along the mouthpiece 69 into the internal chamber C1 and out through the associated flexible tubing or conduit 74 to a conventional device or machine which detects of breathing, sampling of a gas(es) or, alternatively, the associated flexible tubing or conduit 74 can supply a treating gas to the cannula and the mouthpiece 69 which is discharged out though the gas passageway opening 87 and into the patient's mouth when the mouth is open. As with the prior embodiments, a wire 91 facilitates retaining the mouthpiece 69 is a desired adjusted position or orientation relative to a remainder of the cannula and the patient's mouth. The second associated flexible tubing or conduit 76 can be used to supply a desired treating gas, such as oxygen, to the patient via the nasal prong 65, for example.

Figure 22:
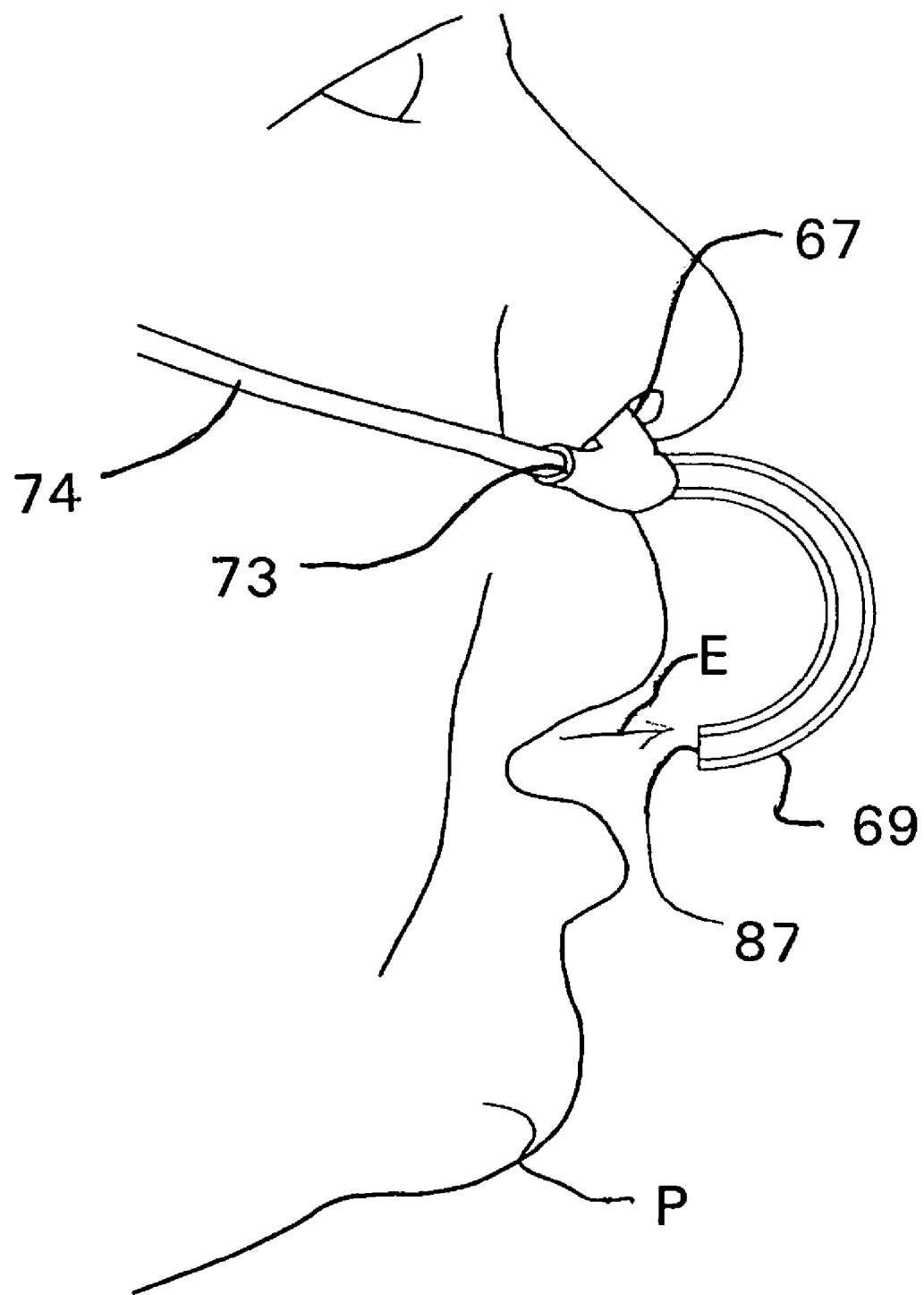
FIG. 22 is a diagrammatic side elevational view showing the proper orientation of the mouthpiece of the cannula of FIG. 20 relative to the open mouth of the patient.

As shown in FIG. 22, a typical desired position or location of the gas passage opening 87 of the cannula is aligned with a central area of the patient's mouth, i.e., it is aligned so as to be coincident with the patient's exhalation/inhalation path E so that the exhalation breath of the patient can readily enter into gas passageway opening 87 and flow along the mouthpiece 69 or, alternatively, a treating gas can readily flow along the mouthpiece 69 and be discharged out through the gas passageway opening 87 and into the patient's mouth when the mouth is open.

Figure 21A:
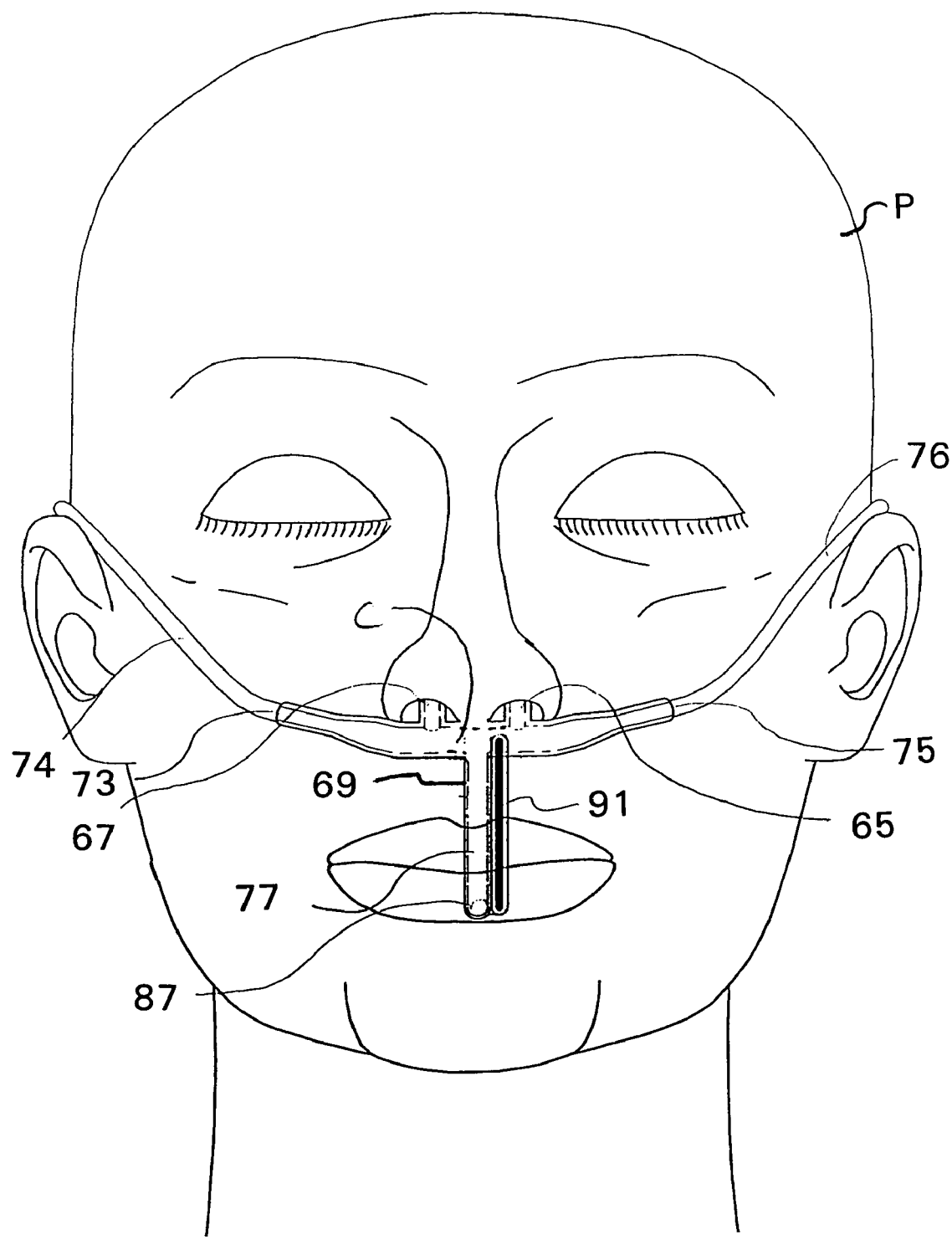
FIG. 21A is a diagrammatic front elevational view, similar to FIG. 21, showing the proper orientation of the mouthpiece of a cannula relative to a closed mouth of the patient but without a septum dividing the internal chamber into two separate passageways.

FIG. 21A is a diagrammatic front elevational view, similar to FIG. 21, showing the proper orientation of the mouthpiece of a cannula relative to a closed mouth of the patient. The only difference between this embodiment, and the embodiment of FIGS. 20 and 21, is that the internal chamber C of the cannula is not divided by a septum into two separate flow paths or passageways. That is, both of the nares 65 and 67 as well as the gas passageway 77 of the mouthpiece 69 all communicate with the undivided central internal chamber C of the cannula. The cannula of FIG. 21A is particularly suited, for example, in detecting a breathing pressure of a patient whether the patient is either mouth breathing, nasal breathing or a combination of both.

Figure 23:
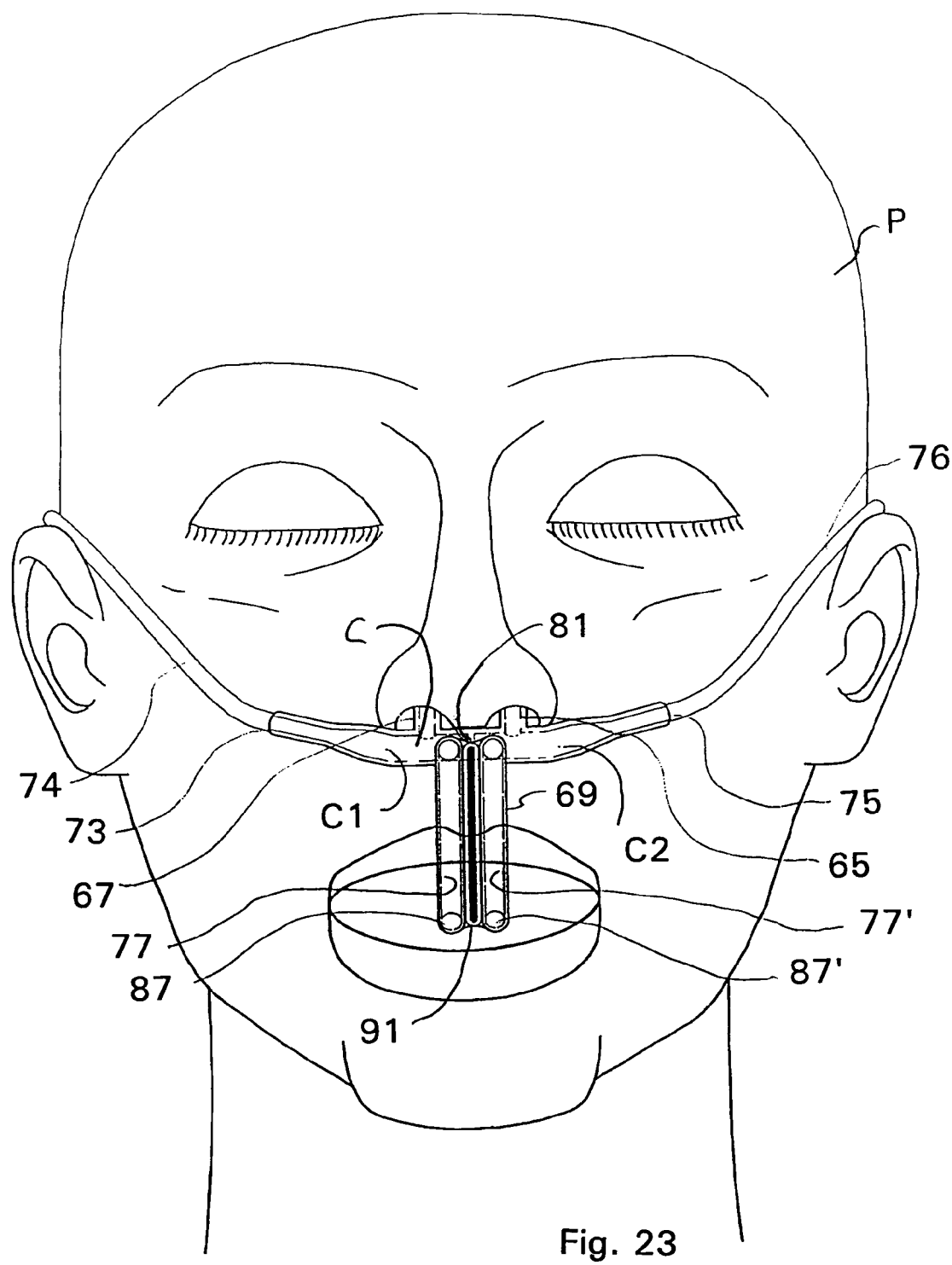
FIG. 23 is a diagrammatic front elevational view showing the proper orientation of a further embodiment of the mouthpiece of the cannula relative to an open mouth of the patient.

With reference to FIG. 23, another embodiment of the cannula is shown which is very similar to the embodiment of FIGS. 20-22 except that the mouthpiece has a pair of side-by-side gas passageways 77 and 77', instead of a single gas passageway 77. Each one of the pair of side-by-side gas passageways 77 and 77' is separated from one another by the retainer passageway which receives a shape retaining member, such as a wire 91.

As shown in this embodiment, the centrally located septum 81 is provided within the internal chamber C of the cannula to form a divided cannula. A first one of the gas passageways 77 communicates with one of the internal compartments or passageways C1 located on one side of the septum 81 while the second one of the gas passageways 77' communicates with the other internal compartment or passageway C2 located on the opposite side of the septum 81. The septum 81 and the wire 91 both lie within a plane which separates or divides the cannula into two substantially equal halves. For example, the cannula of FIG. 23 is suited for detecting breathing pressure of a patient to monitor breathing while simultaneously sampling the carbon dioxide content in the exhaled breath of a patient.

The cannula product of FIG. 23 particularly lends itself to a two-piece construction. That is, the facepiece of the cannula is first manufactured in accordance with the process set forth in FIGS. 15-19 while the mouthpiece 69 is separately extruded as a triple lumen which includes two spaced apart gas passageways with a centrally located retainer passageway. The wire can be either molded during formation of the triple lumen, inside the retainer passageway, so that it is an integral molded or extruded component of the lumen. Alternatively, the lumen can be manufactured without a wire within the retainer passageway and then after the lumen can be cut to a desired length, e.g., about 1½ to about 2½ inches in length. Thereafter, the wire can be assembled or inserted within the central retainer passageway. Finally, a leading end of the mouth piece is then received within the receiving opening of the facepiece and glued or otherwise attached or permanently affixed thereto, in a gas impermeable manner, so that the mouthpiece becomes integral with the remainder of the cannula. It is to be appreciated that the mouthpiece can first be inserted within the receiving opening of the facepiece and glued or otherwise attached or permanently affixed thereto and thereafter the wire can be inserted into the receiving opening to complete manufacture of the cannula.

Figure 24:
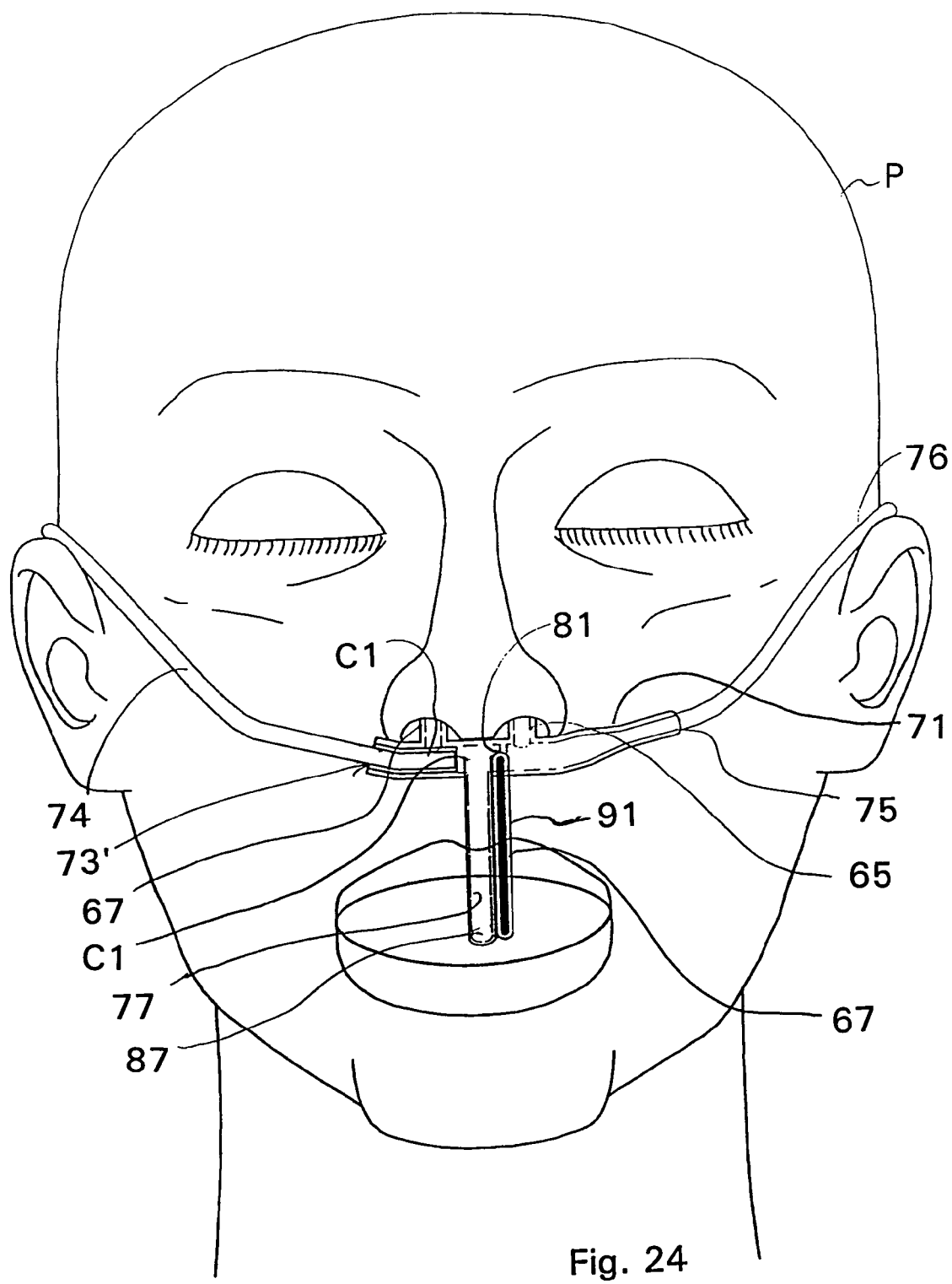
FIG. 24 is a diagrammatic front elevational view showing the proper orientation of a still further embodiment of the mouthpiece of the cannula relative to an open mouth of the patient.
Figure 25:
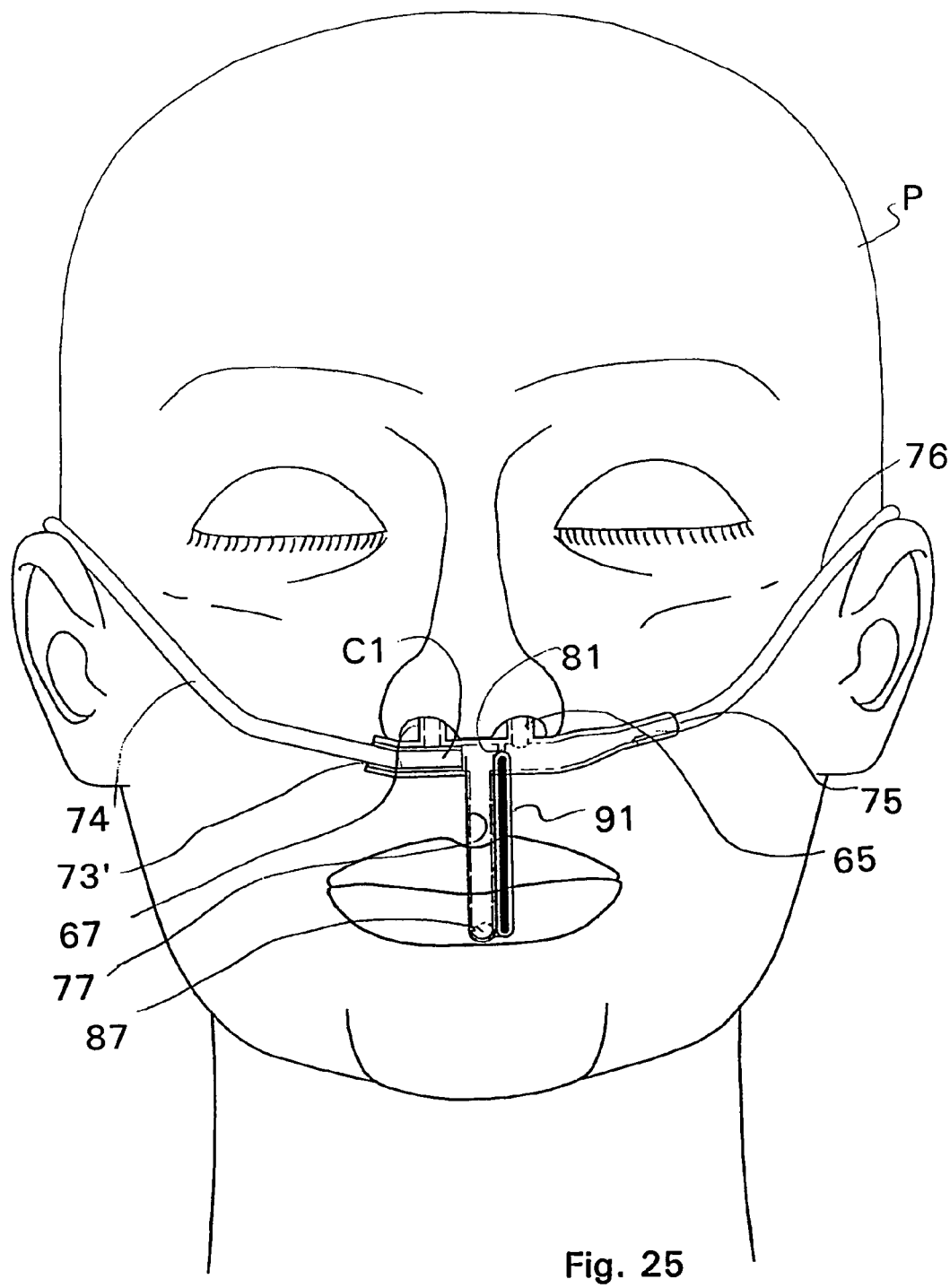
FIG. 25 is a diagrammatic front elevational view, similar to FIG. 24, showing the proper orientation of the mouthpiece of the cannula relative to a closed mouth of the patient.

Turning now to FIGS. 24 and 25, a further modification of the cannula, according to the present invention, is shown. FIG. 24 shows the correct position or location of the gas passageway opening 87 of the mouthpiece 69 relative to the open mouth of the patient, while FIG. 25 shows the correct position or location of the gas passageway opening 87 of the mouthpiece 69 relative to the closed mouth of the patient. According to this embodiment of the cannula, the left side of the main body 71 of the cannula is trimmed or shorten to a position located closely adjacent the left nasal prong 67 (as seen in FIGS. 24 and 25) and the leading end of the associated flexible tubing or conduit 74 is received within the trimmed opening 73' of the cannula. The associated flexible tubing or conduit 74 extends sufficiently into the left side internal compartment or passageway C1 of the cannula such that the leading end of the associated flexible tubing or conduit 74 extends past and seals or blocks off communication with the respective nasal prong 67. Such position of the associated flexible tubing or conduit 74, relative to the opening to the respective nasal prong 67, blocks off gas communication between the associated flexible tubing or conduit 74 and the respective nasal prong 67. The leading end of the associated flexible tubing or conduit 74, however, must not extend too far into the into the left side internal compartment or passageway C1, i.e., extend all the way to the septum 81, so as to blocks off or interrupt gas communication between the associated flexible tubing or conduit 74 and the opening to the gas passageway 77 of the mouthpiece 69. The associated flexible tubing or conduit 74 is typically glued or otherwise affixed or permanently secured within the trimmed opening 73' of the cannula by a suitable adhesive, e.g., MEK. This embodiment results in a cannula in which only one of the nasal prong, nasal prong 65 is able to detect pressure, sample gas or supply a treating gas, for example, while the gas passageway 77 of the mouthpiece 69 is also able to detect pressure, sample gas or supply a treating gas, for example.

Figure 26A:
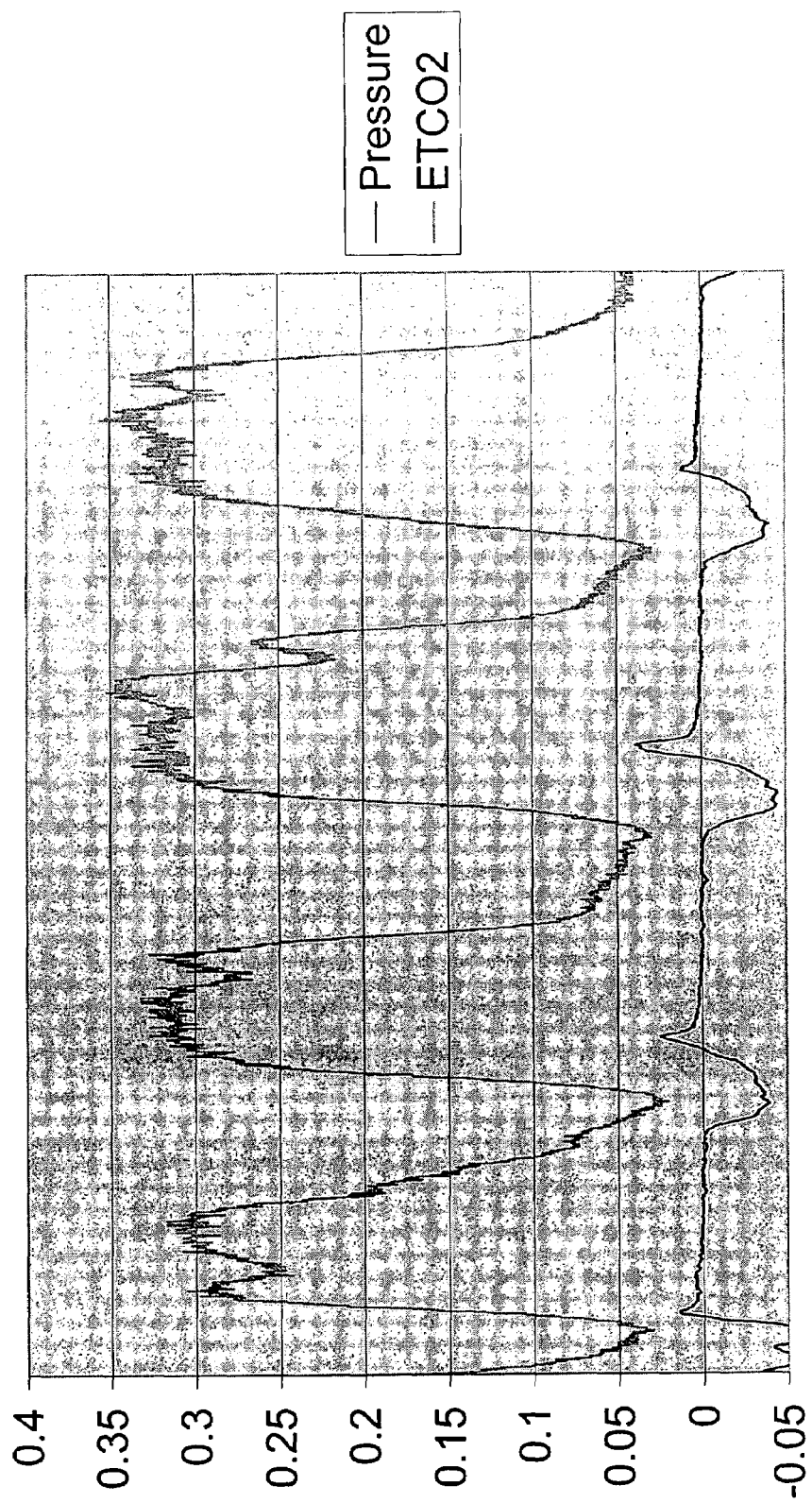
FIG. 26A is a graph displaying test results while the patient inhaled through the nose and exhaled through the mouth, generated by one embodiment of the cannula, showing the detected breathing pressure and end tidal $CO_2$ content in the exhaled breath of a patient.

FIG. 26A is a graph which displays test results of a monitored patient, while the patient inhaled through the nose and exhaled through the mouth, utilizing a cannula generally in accordance with FIG. 23. The cannula detected (1) pressure to determine breathing of the patient (—Pressure) and (2) sampled gas to determine the end tidal $CO_2$ in the blood of the patient by sampling the exhaled gases of the patient (—ETCO2).

Figure 26B:
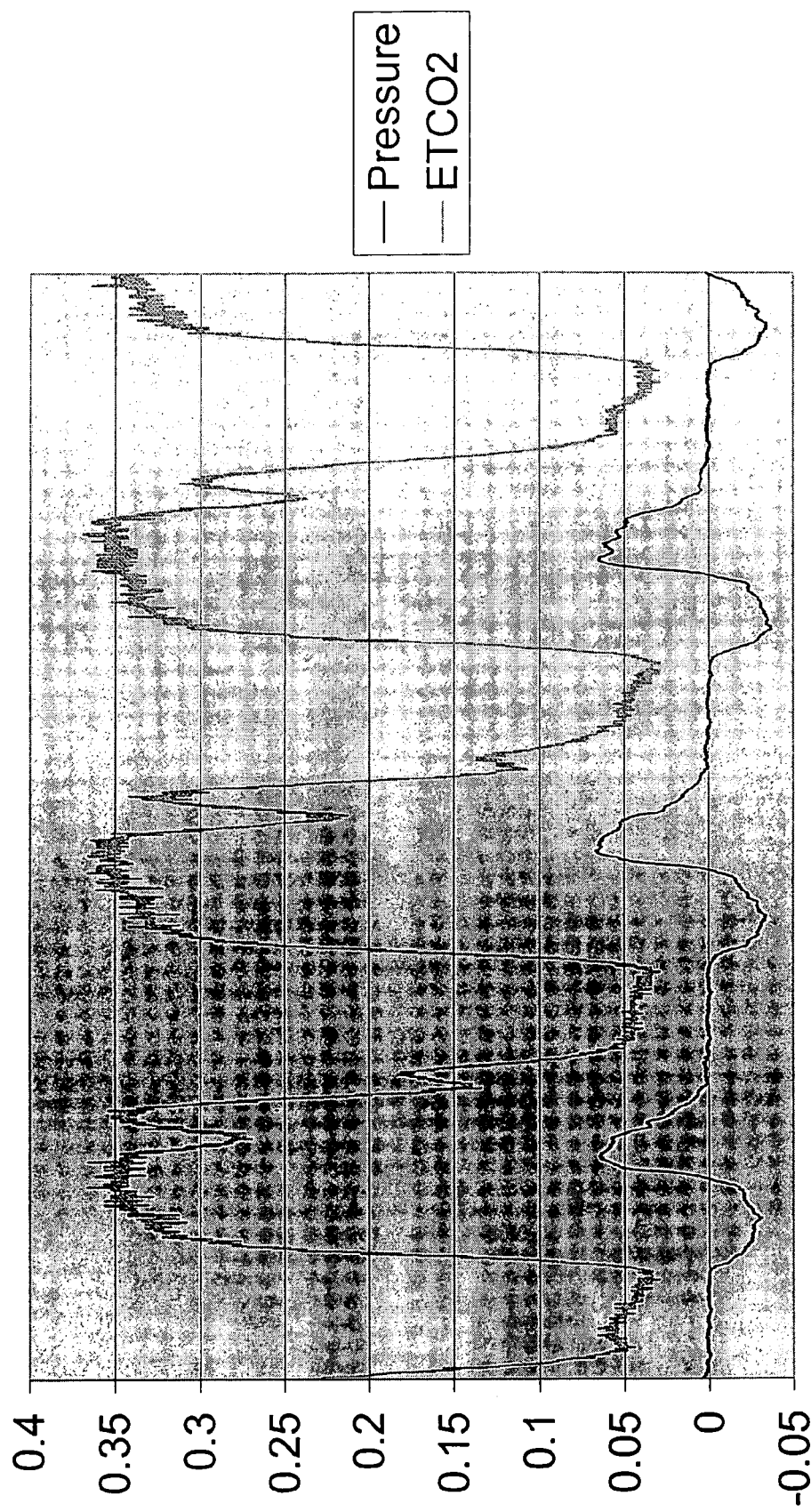
FIG. 26B is an other graph displaying test results while the patient was nose breathing with the mouth open, generated by one embodiment of the cannula, showing the detected breathing pressure and end tidal $CO_2$ content in the exhaled breath of a patient.

FIG. 26B is a further graph which displays test results of a monitored patient, while the patient was nose breathing with the patient's mouth open, utilizing a cannula generally in accordance with FIG. 23. The cannula detected (1) pressure to determine breathing of the patient (—Pressure) and (2) sampled gas to determine the end tidal $CO_2$ in the blood of the patient by sampling the exhaled gases of the patient (—ETCO2).

Figure 26C:
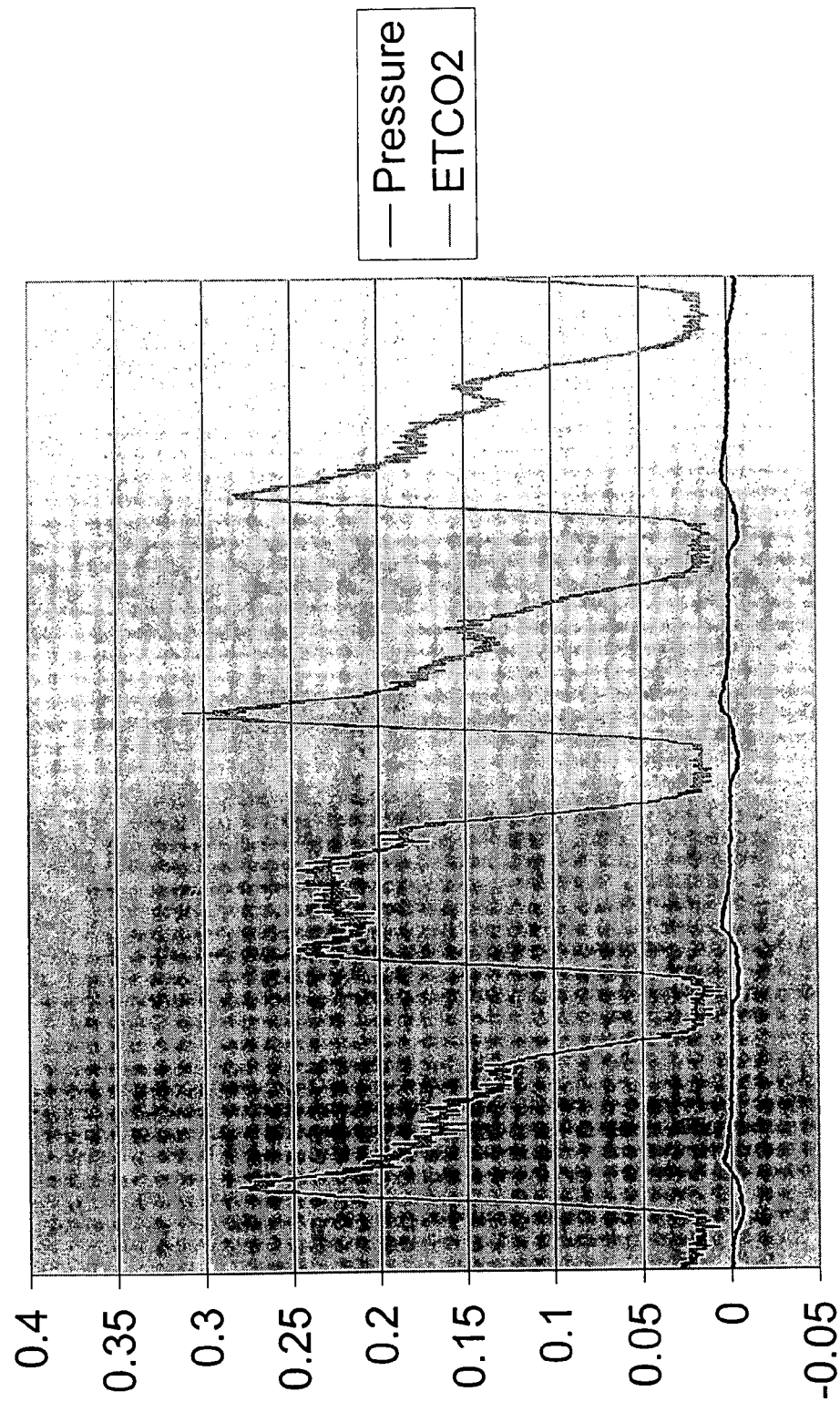
FIG. 26C is a graph displaying test results while the patient was mouth breathing, generated by one embodiment of the cannula, showing the detected breathing pressure and end tidal $CO_2$ content in the exhaled breath of a patient.

FIG. 26C is another graph which displays test results of a monitored patient, while the patient was mouth breathing with the patient's mouth open, utilizing a cannula generally in accordance with FIG. 23. The cannula detected (1) pressure to determine breathing of the patient (—Pressure) and (2) sampled gas to determine the end tidal $CO_2$ in the blood of the patient by sampling the exhaled gases of the patient (—ETCO2).

Figure 27:
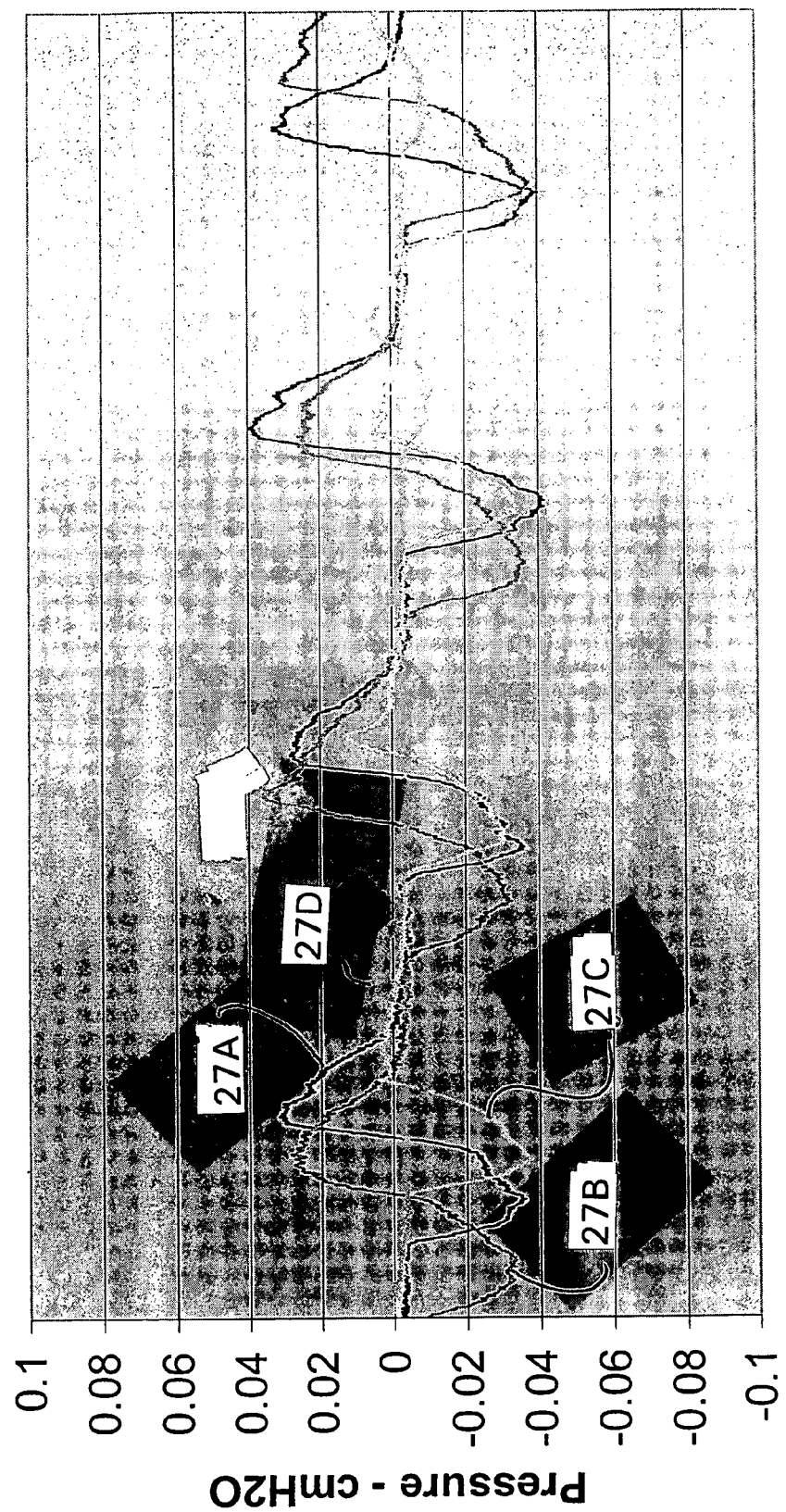
FIG. 27 is a graph displaying test results, generated by an undivided cannula, showing the detected breathing pressure for different breathing styles of the patient.

FIG. 27 is a graph displaying test results, generated by an undivided cannula, showing the detected breathing pressure for different breathing styles of the patient. Graph line 27A show the test results for an undivided cannula with the mouth closed while graph line 27B show the test results for the undivided cannula with the open mouth. Graph line 27C show the test results for the undivided cannula with the patient breathing in through the nose and exhaling out through the mouth while graph line 27D show the test results for the undivided cannula with the patient breathing in and exhaling out through the mouth.

FIG. 28 is a graph displaying additional test results, generated by the nasal port of a dual port oral pressure and separate nasal pressure monitoring cannula, showing the detected breathing pressure for different breathing styles of the patient. Graph line 28A show the test results for the above indicated cannula with the mouth closed while graph line 28B show the test results for the above indicated cannula with the open mouth. Graph line 28C show the test results for the above indicated cannula with the patient breathing in through the nose and exhaling out through the mouth while graph line 28D show the test results for the above indicated cannula with the patient breathing in and exhaling out through the mouth.

In each of the embodiments discussed above, and the actual cannulas and mouthpieces formed by the relative mandrel assemblies, it is generally preferred to have a single dead soft material retaining passage extending along the gas passage of the mouthpiece. In a preferred embodiment of the present invention the retaining passage extends substantially along the length of the gas passage from the free end to the end connected with the main body cannula. The length of the retaining passage permits a similar length of dead soft material which also extends substantially the length of the gas passage, meaning that the retaining passage and dead soft material extends somewhere between about half the length of the gas passage, to somewhere around the full length of the gas passage so as to provide adequate manipulatability and malleability to arrange the mouthpiece of the cannula in a desired manner.

According to this application, the term "nasal cannula facepiece" generally comprises: (1) a hollow main body defining an internal chamber therein and having opposed first and second ends; and (2) at least one and preferably first and second nasal prongs which each communicate with the internal chamber of the main body and define respective first and second nasal prong passages.

The shape retaining member facilitates retaining of an adjusted position, configuration and/or orientation of an opening of the gas passageway with respect to a remainder of the cannula. It is desirable for the shape retaining member to be stiff enough to retain its adjusted shape without returning or creeping back to its prior shape and/or configuration, and the wire will preferably have a gage thickness of between 12 to 32 gage (depending upon the thickness of the mouthpiece, i.e., the thicker the mouthpiece the thicker the gage wire required for that particular application), and more preferably the wire will have a gage thickness of between 18 to 22 gage. The wire is generally coated with an exterior layer to increase its diameter as it is easier to manufacture a larger diameter receiving passageway rather than a smaller diameter receiving passageway.

It is to be appreciated that the mouthpiece could also be injection molded as a single unitary piece or injection molded as two separate pieces, i.e., the facepiece separately molded from the mouthpiece, which are subsequently assembled with one another. Alternatively, the cannula facepiece could also be either injection molded or formed with by polymeric material which is cured. The cannula mouthpiece could be formed by injection molding, by a polymeric material which is cured, or extruded as a separate piece. The facepiece and the mouthpiece are subsequently assembled with one another to form a manufactured cannula.

Since certain changes may be made in the above described improved cannula and method of manufacturing the same, without departing from the spirit and scope of the invention herein involved, it is intended that all of the subject matter of the above description or shown in the accompanying drawings shall be interpreted merely as examples illustrating the inventive concept herein and shall not be construed as limiting the invention.

We claim:

1. A cannula comprising:
   a hollow main body having opposed first and second ends, and the main body defining an internal chamber therein;
   at least a first nasal prong communicating with the internal chamber of the main body and defining a first nasal prong passage;
   a mouthpiece having a gas passageway and a retainer passageway, a first end of the gas passageway communicating with the internal chamber of the main body while a second free end of the mouthpiece having a gas passageway opening therein; and
   an elongate shape retaining member having a first end and a second end, the shape retaining member being received within the retainer passageway with the first end of the shape retaining member located adjacent the main body and the second end of the shape retaining member being located adjacent the second free end of the mouthpiece.

2. The cannula according to claim 1, wherein the cannula has a second nasal prong which communicates with the internal chamber of the main body and defines a second nasal prong passage.

3. The cannula according to claim 2, wherein a septum divides the internal chamber of the main body into separate internal first and second compartments; and the first nasal prong communicates with the first compartment and the second nasal prong communicates with the second compartment.

4. The cannula according to claim 3, wherein the gas passageway of the mouthpiece communicates with first compartment.

5. The cannula according to claim 2, wherein the gas passage and the retainer passageway both generally have substantially similar radii of curvature.

6. The cannula according to claim 2, wherein the gas passageway and the retainer passageway extend substantially side by side with one another along a length of the mouthpiece from the first end to the second free end and have substantially the same radius of curvature.

7. The cannula according to claim 2, wherein the gas passage and the retainer passageway are substantially concentric with one another and the gas passageway has a smaller radius of curvature than a radius of the retainer passageway.

8. The cannula according to claim 2, wherein the gas passageway and the retainer passageway are concentric with one another and the retainer passageway has a smaller radius of curvature than a radius of the gas passageway.

9. The cannula according to in claim 2, wherein the main body, the first and the second nasal prongs and the mouthpiece are all formed as an integral molded structure during a first manufacturing process.

10. The cannula according to in claim 2, wherein the main body and the first and the second nasal prongs are formed as an integral molded structure, during a first manufacturing process, and the mouthpiece is formed during a separate manufacturing process, and the mouthpiece is subsequently attached to main body during a subsequent manufacturing process.

11. The cannula according to in claim 2, wherein the mouthpiece comprises a double lumen which has the gas passageway located side by side with the retainer passageway, and the gas passageway communicates with the internal chamber.

12. The cannula according to in claim 11, wherein the gas passageway has a larger internal cross sectional area than an internal cross sectional area of the retainer passageway.

13. The cannula according to in claim 3, wherein the mouthpiece comprises a triple lumen which has spaced apart first and second gas passageways and the retainer passageway is located between the first and second gas passageways, and the first gas passageway communicates with the first compartment and the second gas passageway communicates with the second separate compartment.

14. The cannula according to in claim 13, wherein the first and second gas passageways have a larger internal cross sectional area than an internal cross sectional area of the retainer passageway.

15. The cannula according to in claim 13, wherein the first and second gas passageways have a smaller internal cross sectional area than an internal cross sectional area of the retainer passageway.

16. The cannula according to in claim 2, wherein the shape retaining member comprises an elongate member made from one of copper, iron, steel, stainless steel, a ferromagnetic material, and a plastic material.

17. A method of manufacturing a nasal cannula comprising the steps of:
    assembling a cannula mandrel assembly comprising separable components with the separable components including a main body forming mandrel, at least one nare forming mandrel, and a mouthpiece forming mandrel;
    heating the assembled cannula mandrel assembly to a desired temperature;
    applying at least one coating of an uncured cannula forming polymeric material to the cannula mandrel assembly to provide a desired material thickness of coating on the cannula mandrel assembly;
    sufficiently curing the coating applied to the cannula mandrel assembly; and
    disassembling the cannula mandrel assembly and withdrawing the at least one nare forming mandrel, and mouthpiece forming mandrel and the main bodyforming mandrel from the manufactured cannula.

18. The method of manufacturing the nasal cannula according to claim 17, further comprising the step of forming the main body forming mandrel as two separate components which are spaced from one another by a gap to define a septum void therebetween.

19. The method of manufacturing the nasal cannula according to claim 17, further comprising the step of providing the mouthpiece forming mandrel with both a retainer prong and a gas passage prong.

20. The method of manufacturing the nasal cannula according to claim 19, further comprising the step of forming the retainer prong and the gas passage prong concentrically with one another and the retainer prong has a larger radius of curvature than a radius of curvature the gas passage prong.

21. The method of manufacturing the nasal cannula according to claim 19, further comprising the step of forming the retainer prong and the gas passage prong concentrically with one another and the retainer prong has a smaller radius of curvature than a radius of curvature the gas passage prong.

22. The method of manufacturing the nasal cannula according to claim 19, further comprising the step of forming the retainer prong and the gas passage prong substantially parallel to one another and the retainer prong has substantially an identical radius of curvature to a radius of curvature the gas passage prong.

23. The method of manufacturing the nasal cannula according to claim 17, further comprising the step of providing the mouthpiece forming mandrel with both a stub and an extension portion for forming a receiving opening in the cannula for receiving a separate mouthpiece.

24. A cannula comprising:
 a hollow main body having opposing openings at a first and second ends;
 a first nasal prong and a second nasal prong defining a respective first and second nasal prong passages communicating with the hollow main body of the cannula;
 a mouthpiece passage for receiving a separate mouthpiece, and the mouthpiece having an elongate shape retaining member within the passages thereto to facilitate adjustment and retention of the mouthpiece in a desired adjusted orientation.

25. The cannula according to in claim 24, further comprising a separate mouthpiece attached to the cannula via the mouthpiece passage.

26. The cannula according to in claim 24, wherein the mouthpiece includes at least a gas passage having a gas inlet communicating with the hollow main body and the shape retaining member is a dead soft material to facilitate adjustment of the gas inlet location.

27. A method of forming a nasal cannula comprising the steps of:
 providing a cannula mandrel assembly, said assembly comprising separable parts including at least one nare forming mandrel, at least one mouthpiece mandrel having an extension, and a main body forming mandrel comprising two separate components defining a void therebetween;
 heating the cannula mandrel assembly to a desired temperature;
 providing an uncured cannula forming polymeric material in flowable state;
 applying at least one coating of the material to the cannula mandrel assembly to provide a desired coating material thickness on the cannula mandrel assembly to form the cannula;
 curing the material coating the cannula mandrel assembly; and
 disassembling the cannula mandrel assembly and withdrawing the at least one nare forming mandrel, the at least one mouthpiece mandrel and extension and the two separate components of the main body forming mandrel from the cannula; and
 attaching a separate mouthpiece to the cannula via an attachment portion formed on the cannula by the mouthpiece mandrel and extension.

28. The method of manufacturing the nasal cannula according to claim 27, further comprising the step of providing the mouthpiece with at least a gas passageway and a retaining passageway.

29. The method of manufacturing the nasal cannula according to claim 27, further comprising the mouthpiece having a separate first and a second gas passages and a single passage for receiving a dead soft material extending substantially the length of the mouthpiece.

* * * * *